US012754665B2

(12) United States Patent
Agarwal et al.

(10) Patent No.: US 12,754,665 B2
(45) Date of Patent: Oct. 6, 2026

(54) ABLATION SYSTEM WITH GRAPHICAL USER INTERFACE

(71) Applicant: BIOSENSE WEBSTER (ISRAEL) LTD., Yokneam (IL)

(72) Inventors: Amit Agarwal, Huntington Beach, CA (US); Ahmed Abdelaal, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 629 days.

(21) Appl. No.: 16/905,487

(22) Filed: Jun. 18, 2020

(65) Prior Publication Data

US 2021/0004145 A1 Jan. 7, 2021

Related U.S. Application Data

(60) Provisional application No. 62/869,516, filed on Jul. 1, 2019.

(51) Int. Cl.
*G06F 3/04845* (2022.01)
*A61B 18/14* (2006.01)
(Continued)

(52) U.S. Cl.
CPC ...... *G06F 3/04845* (2013.01); *A61B 18/1492* (2013.01); *G06F 3/0482* (2013.01); (Continued)

(58) Field of Classification Search
None
See application file for complete search history.

(56) References Cited

U.S. PATENT DOCUMENTS

D123,782 S 12/1940 Ux
3,316,896 A 5/1967 Thomasset
(Continued)

FOREIGN PATENT DOCUMENTS

CN 1225027 A 8/1999
CN 101422637 A 5/2009
(Continued)

OTHER PUBLICATIONS

Shepherd et al. ( WO 2019095020, published May 2019) (Year: 2019).*
(Continued)

*Primary Examiner* — Saptarshi Mazumder
(74) *Attorney, Agent, or Firm* — Calderon Safran & Wright P.C.; Etan S. Chatlynne

(57) ABSTRACT

A graphical user interface (GUI) of a computer system is described herein. The GUI comprises a display (e.g., screen) comprising a first sector and a second sector that may be used to assist a user to perform a surgical intervention, e.g., a cardiac ablation procedure using a catheter having a balloon with electrodes disposed thereon. The first sector may include a menu comprising dialog boxes. The second sector may comprise an image of the balloon and representations of the electrodes. The GUI may also include a processor. The processor may be configured to, e.g., receive inputs from the dialog boxes, change appearances of the dialog boxes, receive inputs from the electrode representations, change appearances of the electrode representations, control irrigation to the balloon, and control power to the electrodes.

21 Claims, 19 Drawing Sheets

(51) Int. Cl.

| | |
|---|---|
| ***G06F 3/0482*** | (2013.01) |
| ***G16H 40/63*** | (2018.01) |
| *A61B 17/00* | (2006.01) |
| *A61B 18/00* | (2006.01) |

(52) U.S. Cl.

CPC .... *G16H 40/63* (2018.01); *A61B 2017/00199* (2013.01); *A61B 2018/0022* (2013.01); *A61B 2018/00375* (2013.01); *A61B 2018/00577* (2013.01); *A61B 2018/00702* (2013.01); *A61B 2018/1407* (2013.01); *A61B 2018/1467* (2013.01); *A61B 2218/002* (2013.01)

(56) References Cited

U.S. PATENT DOCUMENTS

| | | | |
|---|---|---|---|
| 4,232,676 | A | 11/1980 | Herczog |
| 4,276,874 | A | 7/1981 | Wolvek et al. |
| 4,587,975 | A | 5/1986 | Salo et al. |
| 4,709,698 | A | 12/1987 | Johnston et al. |
| 4,805,621 | A | 2/1989 | Heinze et al. |
| 5,085,636 | A | 2/1992 | Burns |
| 5,178,957 | A | 1/1993 | Kolpe et al. |
| 5,391,199 | A | 2/1995 | Ben-Haim |
| 5,429,617 | A | 7/1995 | Hammersmark et al. |
| 5,582,609 | A | 12/1996 | Swanson et al. |
| 5,584,830 | A | 12/1996 | Ladd et al. |
| 5,702,386 | A | 12/1997 | Stern et al. |
| 5,718,241 | A | 2/1998 | Ben-Haim et al. |
| 5,797,903 | A | 8/1998 | Swanson et al. |
| 5,860,974 | A | 1/1999 | Abele |
| 5,971,983 | A | 10/1999 | Lesh |
| 6,012,457 | A | 1/2000 | Lesh |
| 6,024,740 | A | 2/2000 | Lesh et al. |
| 6,042,580 | A | 3/2000 | Simpson |
| 6,091,993 | A | 7/2000 | Bouchier et al. |
| 6,123,718 | A | 9/2000 | Tu et al. |
| 6,142,993 | A | 11/2000 | Whayne et al. |
| 6,164,283 | A | 12/2000 | Lesh |
| 6,171,275 | B1 | 1/2001 | Webster, Jr. |
| 6,176,832 | B1 | 1/2001 | Habu et al. |
| 6,198,974 | B1 | 3/2001 | Webster, Jr. |
| 6,226,542 | B1 | 5/2001 | Reisfeld |
| 6,239,724 | B1 | 5/2001 | Doron et al. |
| 6,301,496 | B1 | 10/2001 | Reisfeld |
| 6,322,558 | B1 | 11/2001 | Taylor et al. |
| 6,322,559 | B1 | 11/2001 | Daulton et al. |
| 6,325,777 | B1 | 12/2001 | Zadno-Azizi et al. |
| 6,332,089 | B1 | 12/2001 | Acker et al. |
| 6,380,957 | B1 * | 4/2002 | Banning ............... G06F 3/0482 715/825 |
| 6,402,740 | B1 | 6/2002 | Ellis et al. |
| D462,389 | S | 9/2002 | Provence et al. |
| 6,471,693 | B1 | 10/2002 | Carroll et al. |
| 6,484,118 | B1 | 11/2002 | Govari |
| 6,522,930 | B1 | 2/2003 | Schaer et al. |
| 6,618,612 | B1 | 9/2003 | Acker et al. |
| 6,656,174 | B1 | 12/2003 | Hegde et al. |
| 6,690,963 | B2 | 2/2004 | Ben-Haim et al. |
| 6,771,996 | B2 | 8/2004 | Bowe et al. |
| 6,814,733 | B2 | 11/2004 | Schwartz et al. |
| 6,892,091 | B1 | 5/2005 | Ben-Haim et al. |
| 6,893,433 | B2 | 5/2005 | Lentz |
| 6,986,744 | B1 | 1/2006 | Krivitski |
| 6,987,995 | B2 | 1/2006 | Drysen |
| 6,997,924 | B2 | 2/2006 | Schwartz et al. |
| 7,066,895 | B2 | 6/2006 | Podany |
| 7,142,903 | B2 | 11/2006 | Rodriguez et al. |
| 7,156,816 | B2 | 1/2007 | Schwartz et al. |
| 7,274,957 | B2 | 9/2007 | Drysen |
| 7,340,307 | B2 | 3/2008 | Maguire et al. |
| 7,377,906 | B2 | 5/2008 | Selkee |
| 7,442,190 | B2 | 10/2008 | Abboud et al. |
| 7,536,218 | B2 | 5/2009 | Govari et al. |
| 7,591,799 | B2 | 9/2009 | Selkee |
| 7,593,760 | B2 | 9/2009 | Rodriguez et al. |
| 7,720,517 | B2 | 5/2010 | Drysen |
| 7,756,576 | B2 | 7/2010 | Levin |
| 7,842,031 | B2 | 11/2010 | Abboud et al. |
| 7,853,302 | B2 | 12/2010 | Rodriguez et al. |
| D635,987 | S | 4/2011 | Mays et al. |
| 8,000,765 | B2 | 8/2011 | Rodriguez et al. |
| 8,021,327 | B2 | 9/2011 | Selkee |
| 8,048,032 | B2 | 11/2011 | Root et al. |
| 8,231,617 | B2 | 7/2012 | Satake |
| 8,267,932 | B2 | 9/2012 | Baxter et al. |
| 8,275,440 | B2 | 9/2012 | Rodriguez et al. |
| 8,348,888 | B2 | 1/2013 | Selkee |
| 8,357,152 | B2 | 1/2013 | Govari et al. |
| D682,289 | S | 5/2013 | Dijulio et al. |
| D682,291 | S | 5/2013 | Baek et al. |
| D690,318 | S | 9/2013 | Kluttz et al. |
| D694,652 | S | 12/2013 | Tompkin |
| 8,641,709 | B2 | 2/2014 | Sauvageau et al. |
| 8,721,590 | B2 | 5/2014 | Seward et al. |
| 8,777,161 | B2 | 7/2014 | Pollock et al. |
| D710,367 | S | 8/2014 | Quattrocchi |
| D716,340 | S | 10/2014 | Bresin et al. |
| 8,852,181 | B2 | 10/2014 | Malecki et al. |
| D720,766 | S | 1/2015 | Mandal et al. |
| D721,379 | S | 1/2015 | Moon et al. |
| D724,618 | S | 3/2015 | Shin |
| 8,974,450 | B2 | 3/2015 | Brannan |
| 8,998,893 | B2 | 4/2015 | Avitall |
| D729,263 | S | 5/2015 | Ahn et al. |
| D734,779 | S | 7/2015 | Dye et al. |
| 9,089,350 | B2 | 7/2015 | Willard |
| D736,780 | S | 8/2015 | Wang |
| 9,126,023 | B1 | 9/2015 | Sahatjian et al. |
| D740,308 | S | 10/2015 | Kim et al. |
| D741,881 | S | 10/2015 | Jihyun et al. |
| D743,424 | S | 11/2015 | Danielyan et al. |
| D744,000 | S | 11/2015 | Villamor et al. |
| 9,173,758 | B2 | 11/2015 | Brister et al. |
| D745,566 | S | 12/2015 | Hellman et al. |
| D747,742 | S | 1/2016 | Fan et al. |
| D750,644 | S | 3/2016 | Bhutani et al. |
| D752,641 | S | 3/2016 | Dye et al. |
| 9,283,034 | B2 | 3/2016 | Katoh et al. |
| 9,289,141 | B2 | 3/2016 | Lowery et al. |
| D753,690 | S | 4/2016 | Vazquez et al. |
| 9,320,631 | B2 | 4/2016 | Moore et al. |
| D755,193 | S | 5/2016 | Sun et al. |
| D757,113 | S | 5/2016 | Hellman et al. |
| 9,345,540 | B2 | 5/2016 | Mallin et al. |
| D759,673 | S | 6/2016 | Looney et al. |
| D759,675 | S | 6/2016 | Looney et al. |
| D760,795 | S | 7/2016 | Barajas et al. |
| D764,500 | S | 8/2016 | Wang |
| D765,709 | S | 9/2016 | Gagnier |
| D767,616 | S | 9/2016 | Jones et al. |
| D768,696 | S | 10/2016 | Gagnier |
| D771,659 | S | 11/2016 | Dye et al. |
| D775,632 | S | 1/2017 | Van Den Berg et al. |
| D783,037 | S | 4/2017 | Hariharan et al. |
| 9,655,677 | B2 | 5/2017 | Salahieh et al. |
| D791,805 | S | 7/2017 | Segars |
| 9,795,442 | B2 | 10/2017 | Salahieh et al. |
| 9,907,610 | B2 | 3/2018 | Beeckler et al. |
| 9,956,035 | B2 | 5/2018 | Govari et al. |
| D856,361 | S | 8/2019 | Sella |
| D859,423 | S | 9/2019 | Kimura |
| D861,717 | S | 10/2019 | Brekke et al. |
| D873,294 | S | 1/2020 | Anzures et al. |
| 10,668,258 | B1 | 6/2020 | Calhoun et al. |
| 10,688,278 | B2 | 6/2020 | Beeckler et al. |
| D895,638 | S | 9/2020 | Van Den Berg et al. |
| D914,717 | S | 3/2021 | Mensinger et al. |
| D928,833 | S | 8/2021 | Luo et al. |
| D930,700 | S | 9/2021 | Arena et al. |
| D931,875 | S | 9/2021 | Dailey et al. |
| D936,665 | S | 11/2021 | Ozeri et al. |
| D941,321 | S | 1/2022 | Nishikawa |
| D942,480 | S | 2/2022 | Onodi-Wolff et al. |

(56) References Cited

U.S. PATENT DOCUMENTS

D945,444 S 3/2022 Gu et al.
D946,006 S 3/2022 Chaudhary
D948,534 S 4/2022 Bessette et al.
D955,429 S 6/2022 Xie et al.
D968,421 S 11/2022 Agarwal et al.
D968,422 S 11/2022 Agarwal et al.
D969,138 S 11/2022 Agarwal et al.
D1,096,761 S 10/2025 Boutoussov et al.
12,462,468 B2 11/2025 Bharadwaj et al.
2001/0031961 A1 10/2001 Hooven
2002/0002369 A1 1/2002 Hood
2002/0065455 A1 5/2002 Ben-Haim et al.
2002/0068931 A1 6/2002 Wong et al.
2002/0077627 A1 6/2002 Johnson et al.
2002/0160134 A1 10/2002 Ogushi et al.
2003/0018327 A1 1/2003 Truckai et al.
2003/0028183 A1 2/2003 Sanchez et al.
2003/0050637 A1 3/2003 Maguire et al.
2003/0060820 A1 3/2003 Maguire et al.
2003/0120150 A1 6/2003 Govari
2003/0144658 A1 7/2003 Schwartz et al.
2003/0178032 A1 9/2003 Ingle et al.
2004/0068178 A1 4/2004 Govari
2004/0122445 A1 6/2004 Butler et al.
2004/0147920 A1 7/2004 Keidar et al.
2004/0225285 A1 11/2004 Gibson
2005/0059862 A1 3/2005 Phan
2005/0070887 A1 3/2005 Taimisto et al.
2005/0119686 A1 6/2005 Clubb
2006/0013595 A1 1/2006 Trezza et al.
2006/0106375 A1 5/2006 Werneth et al.
2006/0135953 A1 6/2006 Kania et al.
2007/0005092 A1 1/2007 Godin et al.
2007/0071792 A1 3/2007 Varner et al.
2007/0080322 A1 4/2007 Walba
2007/0083194 A1 4/2007 Kunis et al.
2007/0276212 A1 11/2007 Fuimaono et al.
2007/0287994 A1 12/2007 Patel
2008/0018891 A1 1/2008 Hell et al.
2008/0021313 A1 1/2008 Eidenschink et al.
2008/0051707 A1 2/2008 Phan et al.
2008/0140072 A1 6/2008 Stangenes et al.
2008/0161797 A1 7/2008 Wang et al.
2008/0183132 A1 7/2008 Davies et al.
2008/0188912 A1 8/2008 Stone et al.
2008/0202637 A1 8/2008 Hector et al.
2008/0208186 A1 8/2008 Slater
2008/0249463 A1 10/2008 Pappone et al.
2008/0249527 A1 10/2008 Couture
2008/0262489 A1 10/2008 Steinke
2008/0281312 A1 11/2008 Werneth et al.
2009/0163890 A1 6/2009 Clifford et al.
2009/0171274 A1 7/2009 Harlev et al.
2009/0182318 A1 7/2009 Abboud et al.
2009/0270850 A1 10/2009 Zhou et al.
2010/0060604 A1 3/2010 Zwart et al.
2010/0069836 A1 3/2010 Satake
2010/0114269 A1 5/2010 Wittenberger et al.
2010/0160906 A1 6/2010 Jarrard
2010/0204560 A1 8/2010 Salahieh et al.
2010/0256627 A1 10/2010 Ma et al.
2010/0256629 A1 10/2010 Wylie et al.
2010/0324552 A1 12/2010 Kauphusman et al.
2011/0118632 A1 5/2011 Sinelnikov et al.
2011/0130648 A1 6/2011 Beeckler et al.
2011/0282338 A1 11/2011 Fojtik
2011/0295248 A1 12/2011 Wallace et al.
2011/0301587 A1 12/2011 Deem et al.
2011/0313286 A1 12/2011 Whayne et al.
2012/0019107 A1 1/2012 Gabl et al.
2012/0029511 A1 2/2012 Smith et al.
2012/0065503 A1 3/2012 Rogers et al.
2012/0071870 A1 3/2012 Salahieh et al.
2012/0079427 A1 3/2012 Carmichael et al.
2012/0101413 A1 4/2012 Beetel et al.
2012/0101538 A1 4/2012 Ballakur et al.
2012/0143177 A1 6/2012 Avitall
2012/0143293 A1 6/2012 Mauch et al.
2012/0191079 A1 7/2012 Moll et al.
2012/0209260 A1 8/2012 Lambert et al.
2013/0085360 A1 4/2013 Grunewald
2013/0090649 A1 4/2013 Smith et al.
2013/0109982 A1 5/2013 Sato et al.
2013/0150693 A1 6/2013 D'Angelo et al.
2013/0165916 A1 6/2013 Mathur et al.
2013/0165925 A1 6/2013 Mathur et al.
2013/0165941 A1 6/2013 Murphy
2013/0165990 A1 6/2013 Mathur et al.
2013/0169624 A1 7/2013 Bourier et al.
2013/0184702 A1 7/2013 Neal, II et al.
2013/0261692 A1 10/2013 Cardinal et al.
2013/0274562 A1 10/2013 Ghaffari et al.
2013/0274658 A1 10/2013 Steinke et al.
2013/0282084 A1 10/2013 Mathur et al.
2013/0318439 A1 11/2013 Landis et al.
2014/0012242 A1 1/2014 Lee et al.
2014/0018788 A1 1/2014 Engelman et al.
2014/0031813 A1 1/2014 Tellio et al.
2014/0058197 A1 2/2014 Salahieh et al.
2014/0121470 A1 5/2014 Scharf et al.
2014/0148805 A1 5/2014 Stewart et al.
2014/0227437 A1 8/2014 Deboer et al.
2014/0243821 A1 8/2014 Salahieh et al.
2014/0257280 A1 9/2014 Hanson et al.
2014/0275993 A1 9/2014 Ballakur
2014/0276756 A1 9/2014 Hill
2014/0276811 A1 9/2014 Koblish et al.
2014/0288546 A1 9/2014 Sherman et al.
2014/0330266 A1* 11/2014 Thompson ......... A61B 18/1206
606/34
2014/0357956 A1 12/2014 Salahieh et al.
2014/0378803 A1 12/2014 Geistert et al.
2015/0005799 A1 1/2015 Lindquist et al.
2015/0018818 A1 1/2015 Willard et al.
2015/0025532 A1 1/2015 Hanson et al.
2015/0025533 A1 1/2015 Groff et al.
2015/0057655 A1 2/2015 Osypka
2015/0067512 A1 3/2015 Roswell
2015/0080883 A1 3/2015 Haverkost et al.
2015/0105774 A1 4/2015 Lindquist et al.
2015/0112256 A1 4/2015 Byrne et al.
2015/0112321 A1 4/2015 Cadouri
2015/0119875 A1 4/2015 Fischell et al.
2015/0119877 A1 4/2015 Jameson et al.
2015/0141982 A1 5/2015 Lee
2015/0157382 A1 6/2015 Avitall et al.
2015/0216591 A1 8/2015 Cao et al.
2015/0216650 A1 8/2015 Shaltis
2015/0265329 A1 9/2015 Lalonde et al.
2015/0265339 A1 9/2015 Lindquist et al.
2015/0265812 A1 9/2015 Lalonde
2015/0272667 A1 10/2015 Govari et al.
2015/0327805 A1 11/2015 Ben-Haim
2015/0341752 A1 11/2015 Flynn
2016/0000499 A1 1/2016 Lennox et al.
2016/0051321 A1 2/2016 Salahieh et al.
2016/0085431 A1 3/2016 Kim et al.
2016/0106499 A1 4/2016 Ogata et al.
2016/0166306 A1 6/2016 Pageard
2016/0175041 A1 6/2016 Govari et al.
2016/0183877 A1 6/2016 Williams et al.
2016/0196635 A1 7/2016 Cho et al.
2016/0256305 A1 9/2016 Longo et al.
2016/0374748 A9 12/2016 Salahieh et al.
2017/0042614 A1 2/2017 Salahieh et al.
2017/0042615 A1 2/2017 Salahieh et al.
2017/0080192 A1 3/2017 Giasolli et al.
2017/0100195 A1 4/2017 Velusamy
2017/0143359 A1 5/2017 Nguyen et al.
2017/0164464 A1 6/2017 Weinkam et al.
2017/0311829 A1 11/2017 Beeckler et al.
2017/0311893 A1 11/2017 Beeckler et al.
2017/0312022 A1 11/2017 Beeckler et al.
2017/0325900 A1 11/2017 Harlev et al.

(56) References Cited

U.S. PATENT DOCUMENTS

| | | | | |
|---|---|---|---|---|
| 2017/0347896 | A1 | 12/2017 | Keyes et al. | |
| 2017/0348049 | A1 | 12/2017 | Vrba et al. | |
| 2017/0354467 | A1 | 12/2017 | Rankin et al. | |
| 2018/0074693 | A1 | 3/2018 | Jones et al. | |
| 2018/0092688 | A1 | 4/2018 | Tegg | |
| 2018/0110562 | A1 | 4/2018 | Govari et al. | |
| 2018/0125575 | A1 | 5/2018 | Schwartz et al. | |
| 2018/0161093 | A1 | 6/2018 | Basu et al. | |
| 2018/0256247 | A1 | 9/2018 | Govari et al. | |
| 2018/0280080 | A1 | 10/2018 | Govari et al. | |
| 2018/0333162 | A1 | 11/2018 | Saab | |
| 2018/0368927 | A1* | 12/2018 | Lyons | A61B 34/25 |
| 2019/0059818 | A1 | 2/2019 | Herrera et al. | |
| 2019/0060622 | A1 | 2/2019 | Beeckler | |
| 2019/0117303 | A1 | 4/2019 | Claude et al. | |
| 2019/0143079 | A1 | 5/2019 | Beeckler et al. | |
| 2019/0175262 | A1 | 6/2019 | Govari et al. | |
| 2019/0175263 | A1 | 6/2019 | Altmann et al. | |
| 2019/0183567 | A1 | 6/2019 | Govari et al. | |
| 2019/0201669 | A1 | 7/2019 | Govari et al. | |
| 2019/0217065 | A1 | 7/2019 | Govari et al. | |
| 2019/0297441 | A1 | 9/2019 | Dehe et al. | |
| 2019/0298441 | A1 | 10/2019 | Clark et al. | |
| 2019/0365451 | A1 | 12/2019 | Jung, Jr. | |
| 2020/0001054 | A1 | 1/2020 | Jimenez et al. | |
| 2020/0008869 | A1 | 1/2020 | Byrd | |
| 2020/0015693 | A1 | 1/2020 | Beeckler et al. | |
| 2020/0046422 | A1 | 2/2020 | Bishara et al. | |
| 2020/0085497 | A1 | 3/2020 | Zhang et al. | |
| 2020/0155226 | A1 | 5/2020 | Valls et al. | |
| 2021/0169567 | A1 | 6/2021 | Govari et al. | |

FOREIGN PATENT DOCUMENTS

| | | | |
|---|---|---|---|
| CN | 102106752 | A | 6/2011 |
| CN | 102271607 | A | 12/2011 |
| CN | 102458566 | A | 5/2012 |
| CN | 103118613 | A | 5/2013 |
| CN | 203539434 | U | 4/2014 |
| CN | 104244856 | A | 12/2014 |
| CN | 104546117 | A | 4/2015 |
| CN | 104939916 | A | 9/2015 |
| CN | 105105844 | A | 12/2015 |
| CN | 105473091 | A | 4/2016 |
| CN | 105473093 | A | 4/2016 |
| CN | 106572842 | A | 4/2017 |
| CN | 107970065 | A | 5/2018 |
| CN | 108175400 | A | 6/2018 |
| CN | 210872009 | U | 6/2020 |
| EM | EU0025675860003 | S | 11/2014 |
| EM | EU0049190090001 | S | 5/2018 |
| EM | EU0049190090002 | S | 5/2018 |
| EP | 0779059 | A1 | 6/1997 |
| EP | 1790304 | A2 | 5/2007 |
| EP | 2749214 | A1 | 7/2014 |
| EP | 2865350 | A2 | 4/2015 |
| EP | 2875790 | A2 | 5/2015 |
| EP | 3199118 | A1 | 8/2017 |
| EP | 3238646 | A2 | 11/2017 |
| EP | 3238648 | A1 | 11/2017 |
| EP | 3251622 | A1 | 12/2017 |
| EP | 3300680 | A1 | 4/2018 |
| EP | 3315087 | A1 | 5/2018 |
| EP | 3332727 | A2 | 6/2018 |
| EP | 3571983 | A2 | 11/2019 |
| EP | 3572024 | A1 | 11/2019 |
| EP | 3586778 | A1 | 1/2020 |
| EP | 3653153 | A1 | 5/2020 |
| JP | H0314121 | A | 1/1991 |
| JP | H06261951 | A | 9/1994 |
| JP | H07110032 | B2 | 11/1995 |
| JP | H1176233 | A | 3/1999 |
| JP | H11327735 | A | 11/1999 |
| JP | 2000504242 | A | 4/2000 |
| JP | 2002336266 | A | 11/2002 |
| JP | 2004504314 | A | 2/2004 |
| JP | 2005052424 | A | 3/2005 |
| JP | 2008538986 | A | 11/2008 |
| JP | 2009261609 | A | 11/2009 |
| JP | 2010507404 | A | 3/2010 |
| JP | 2010088697 | A | 4/2010 |
| JP | 2012024156 | A | 2/2012 |
| JP | 2012508083 | A | 4/2012 |
| JP | 2013013726 | A | 1/2013 |
| JP | 2013078587 | A | 5/2013 |
| JP | 2013529109 | A | 7/2013 |
| JP | 2014509218 | A | 4/2014 |
| JP | 2014529419 | A | 11/2014 |
| JP | 2015503365 | A | 2/2015 |
| JP | 2015100706 | A | 6/2015 |
| JP | 2015112113 | A | 6/2015 |
| JP | 2015112114 | A | 6/2015 |
| JP | 2015518776 | A | 7/2015 |
| JP | 2016093502 | A | 5/2016 |
| JP | 2016515442 | A | 5/2016 |
| JP | 2016116863 | A | 6/2016 |
| JP | 2016534842 | A | 11/2016 |
| JP | 2017202305 | A | 11/2017 |
| JP | 2017202306 | A | 11/2017 |
| JP | 2018075365 | A | 5/2018 |
| JP | D1678854 | | 2/2021 |
| KR | 300663440 | S | 10/2012 |
| KR | 3009948880027 | S | 2/2019 |
| KR | 301061710 | S | 6/2020 |
| RU | 2443390 | C1 | 2/2012 |
| WO | 9605768 | A1 | 2/1996 |
| WO | 0056237 | A2 | 9/2000 |
| WO | 02102231 | A2 | 12/2002 |
| WO | 2005041748 | A2 | 5/2005 |
| WO | 2006055654 | A1 | 5/2006 |
| WO | 2008049087 | A2 | 4/2008 |
| WO | 2011143468 | A2 | 11/2011 |
| WO | 2013049601 | A2 | 4/2013 |
| WO | 2013052919 | A2 | 4/2013 |
| WO | 2013154776 | A2 | 10/2013 |
| WO | 2014123983 | A2 | 8/2014 |
| WO | 2014168987 | A1 | 10/2014 |
| WO | 2015049784 | A1 | 4/2015 |
| WO | 2015200518 | A1 | 12/2015 |
| WO | 2016084215 | A1 | 6/2016 |
| WO | 2016183337 | A2 | 11/2016 |
| WO | 2016210437 | A1 | 12/2016 |
| WO | 2017024306 | A1 | 2/2017 |
| WO | 2017087549 | A1 | 5/2017 |
| WO | 2017163400 | A1 | 9/2017 |
| WO | 2018106569 | A1 | 6/2018 |
| WO | 2018129133 | A1 | 7/2018 |
| WO | WO2019095020 | * | 5/2019 |
| WO | 2019156195 | A1 | 8/2019 |

OTHER PUBLICATIONS

Extended European Search Report for European Application No. EP20195648.9, mailed on Feb. 12, 2021, 8 pages.

Copending U.S. Appl. No. 15/452,843, filed Mar. 8, 2017, 24 pages.

Copending U.S. Appl. No. 16/036,710, filed Jul. 16, 2018, 35 pages.

Extended European Search Report for Application No. EP17168393.1 mailed on Dec. 15, 2017, 12 pages.

Extended European Search Report for Application No. EP17168513.4 mailed on Sep. 18, 2017, 11 pages.

Extended European Search Report for European Application No. 17201434.2, mailed on Feb. 1, 2018, 9 pages.

Extended European Search Report for European Application No. EP15201723.2, mailed on May 11, 2016, 7 pages.

Extended European Search Report for European Application No. EP17168518.3, mailed on Sep. 20, 2017, 9 pages.

Extended European Search Report for European Application No. EP17173893.3, mailed on Nov. 6, 2017, 8 pages.

Extended European Search Report for European Application No. EP17205876.0, mailed on Jun. 1, 2018, 13 pages.

Extended European Search Report for European Application No. EP20153872.5, mailed on May 7, 2020, 8 pages.

(56) References Cited

OTHER PUBLICATIONS

International Search Report and Written Opinion for Application No. PCT/IB2019/056381, mailed on Dec. 17, 2019, 10 pages.
International Search Report and Written Opinion for Application No. PCT/IB2019/052313, mailed on Jul. 22, 2019, 08 pages.
Partial European Search Report for Application No. EP17168393.1 mailed on Sep. 13, 2017, 13 pages.
Partial European Search Report for European Application No. EP17205876.0, mailed on Feb. 22, 2018, 10 pages.
European Search Report for European Application No. 19183327, mailed on Nov. 21, 2019, 8 pages.
Youtube, "Intensity™ CX4 Professional E-Stim/Ultrasound Combo", Dec. 22, 2015, Retrieved from internet [https://www.youtube.com/watch?v=76s1QKMWJME], retrieved on Nov. 19, 2020, 1 page.
YouTube, "New Interface TactiCath Contact Force Ablation Catheter", Nov. 26, 2013, retrieved from internet [https://www.youtube.com/watch?v=aYvYO8Hpylg], retrieved on Nov. 19, 2020, 1 page.
Extended European Search Report for European Application No. EP19177365.4, mailed on Nov. 8, 2019, 7 pages.
David E. Haines et al., "The Promise of Pulsed Field Ablation," Dec. 2019, vol. 19 (12), pp. 10.
Compounding Solutions, "PEBA RO Compounds", Nov. 17, 2017 (Year: 2017), 1 page.
Demetrius Lopes, Balloon Design and Performance: Presentation of various types of balloons on the market. Attached. Also available at: https://www.neurovascularexchange.com/media/slides/210/balloon-design-and-performance-presentation-of-various-types-of-balloons-on-the-market.pdf, 2016, 80 pages.
Foster, "Foster Corporation Introduces Newest ProPellTM "T" Translucent Compounds", Sep. 13, 2018 (Year: 2018), 3 pages.
Foster, "Foster ProPellTM "T" Low Friction Compounds", 2018 (Year: 2018), 2 pages.
Medtronic, Hyper Occlusion Balloon Portfolio. Attached. Also Available at: https://www.linnc.com/content/download/125103/2591577/version/1/file/Hyper+Balloon+Brochure+LR.pdf, 2017, 3 pages.
Guojun, C., "Fundamentals of Computer Applications, "Jinan University Press, 2008, 29 pages.
Okura, M., et al., "Dreamweaver CS3 Masterbook for Windows & Macintosh, "Mainichi Communications Inc, 2007, 12 pages.
Casella et al., "Ablation Index as a Predictor of Long-term Efficacy in Premature Ventricular Complex Ablation: A Regional Target Value Analysis, "Heart Rhythm Society, 2019, vol. 16 (6), pp. 888-895.
Das et al., "Ablation Index, a Novel Marker of Ablation Lesion Quality: Prediction of Pulmonary Vein Reconnection at Repeat Electrophysiology Study and Regional Differences in Target Values, "Europace, 2017, vol. 19, pp. 775-783.
Dorobantu et al., "Oral Anticoagulation During Atrial Fibrillation Ablation: Facts and Controversies, "Cor et Vasa, 2013, vol. 55 (2), pp. e101-e106.
Evgenieva A.P" Russian Language Dictionary" M. Russian Language, 1985-1988, pp. 280-284.
Fornell., "Multi-Electrode RF Balloon Efficient for Acute Pulmonary Vein Isolation," Diagnostic and Interventional Cardiology, 2017, 8 pages.
Honarbakhsh., et al., "Radiofrequency Balloon Catheter Ablation For Paroxysmal Atrial Fibrillation, Radiance Study-a UK Experience," EP Europace, 2017, vol. 19, p. 1 Pages.
Matthew., AF Symposium 2017: First-in-Man Study Shows Promising Results with a Multi-Electrode Radiofrequency Balloon for Paroxysmal AF Treatment, Jan. 20, 2017, 2 Pages.
Nagashima., et al., "Hot Balloon Versus Cryoballoon Ablation for Atrial Fibrillation," Circulation: Arrhythmia and Electrophysiology, May 2018, vol. 11(5):e005861, pp. 1-9.
Napoli., "For Atrial Fibrillation Ablation, Newer Anticoagulant Reduces Major Bleeds," American College of Cardiology, 2017, pp. 1-4.
Okano., et al., "Wire Perforation Causing Cardiopulmonary Arrest During Radiofrequency Hot Balloon Ablation for pulmonary Vein Isolation," Journal of Cardiology Cases, Feb. 15, 2019, vol. 19(5), pp. 169-172.
Reddy., et al., "Balloon Catheter Ablation to Treat Paroxysmal Atrial Fibrillation: What is the Level of Pulmonary venous Isolation," Heart Rhythm, Mar. 2008, vol. 5(3), pp. 353-360.
Volin., et al., "Russian defining dictionary," Terra-Terra, 1996.
Winkle., et al., "Atrial Fibrillation Ablation Using Open-Irrigated Tip Radiofrequency: Experience with Intraprocedural Activated Clotting Times 210 Seconds," Jun. 2014, Heart Rhythm Society, vol. 11(6), pp. 963-968.

* cited by examiner

ABLATION SYSTEM WITH GRAPHICAL USER INTERFACE

CROSS REFERENCE TO COPENDING APPLICATIONS

The present application claims priority under 35 U.S.C. § 119 to U.S. Provisional Patent Application No. 62/869,516, filed Jul. 1, 2019. This application also relates to subject matter described in U.S. patent application Ser. No. 15/360,966, filed Nov. 23, 2016, U.S. patent application Ser. No. 15/939,154, filed Mar. 28, 2018, U.S. Design patent application Ser. No. 29/693,273, filed May 31, 2019, U.S. Design patent application Ser. No. 29/693,281, filed May 31, 2019, and U.S. Design patent application Ser. No. 29/693,296, filed May 31, 2019. The entire contents of these applications are incorporated by reference herein in their entirety.

FIELD

The subject matter disclosed herein relates to ablation systems, particularly those that include a catheter capable of ablating cardiac tissue and a graphical user interface system to assist in performing the ablation.

BACKGROUND

Ablation of cardiac tissue has been used to treat cardiac arrhythmias. Ablative energies are typically provided to cardiac tissue by a tip portion which can deliver ablative energy alongside the tissue to be ablated. Some of these catheters administer ablative energy from various electrodes three-dimensional structures. Ablative procedures incorporating such catheters may be visualized using, e.g., fluoroscopy.

SUMMARY OF THE DISCLOSURE

A graphical user interface (GUI) of a computer system is described herein. The GUI comprises a display (e.g., screen) comprising a first sector and a second sector. The first sector may include a menu comprising a first dialog box, a second dialog box, and an ultimate dialog box. The second sector may comprise an image of a balloon including a plurality of electrode representations including a first-electrode representation. The GUI may also include a processor. The processor may be configured to receive a first first-dialog-box input from the first dialog box, change an appearance of the first dialog box in response to receiving the first first-dialog-box input, change an appearance of the second dialog box, receive a first first-electrode input from the first-electrode representation, and change the first-electrode representation upon receiving the first first-electrode input. The processor may also be configured to change the image of the balloon in response to receiving the first first-dialog box input.

The plurality of electrode representations may include indicators to assist in distinguishing them from each other. For example, at least one of the plurality of electrode representations may include a shape indicator, an alphanumeric indicator, or both.

The processor may also be configured to change the appearance of the second dialog box in response to receiving the first first-dialog box input. The processor may also be configured to change the appearance of the second dialog box in response to receiving a first second-dialog box input. The processor may also be configured to change an appearance of the first dialog box in response to receiving the first second-dialog-box input. The processor may also be configured to prevent the change in appearance of the second dialog box before receiving the first first-dialog box input. The processor may also be configured to receive a second second-dialog box input from the second dialog box and further change the appearance of the second dialog box in response to receiving the second second-dialog-box input. The processor may also be configured to change the appearance of the plurality of electrode representations in response to receiving the second second-dialog box input. The processor may also be configured to activate at least one of a plurality of electrodes connected to the processor in response to receiving an ultimate-dialog-box input, the plurality of electrodes comprising a first electrode. The processor may also be configured to display a measure of progress (e.g., a timer) in response to receiving the ultimate-dialog-box input. The processor may also be configured to cause the display to display a global power setting in response to receiving the ultimate-dialog-box input. The processor may also be configured to receive a second first-electrode input from the first-electrode representation and change the first-electrode representation upon receiving the second first-electrode input. The processor may also be configured to receive a third first-electrode input from the first electrode representation and change the first-electrode representation upon receiving the third first-electrode input. The processor may also be configured to change the appearance of the second dialog box in response to receiving at least one of the first first-electrode input, the second first-electrode input, and the third first-electrode input.

As one example, the first first-dialog-box input may comprise a command to the processor to activate a pump connected to the processor. As another example, the first first-electrode input may comprise a command to designate a position of the first electrode relative to at least another electrode of the plurality of electrodes. As another example, the second first-electrode input may comprise a command to prevent the first electrode from being activated.

In further embodiments, the plurality of electrodes may comprise a second electrode and the plurality of electrode representations may comprise a second-electrode representation. As such, the processor may be configured to receive a first second-electrode input from the second-electrode representation and change the second-electrode representation upon receiving the first second-electrode input. Further, the processor may be configured to receive a second second-electrode input from the second-electrode representation and change the second-electrode representation upon receiving the second second-electrode input. Further the processor may be configured to receive a third second-electrode input from the second-electrode representation and change the second-electrode representation upon receiving the third second-electrode input.

In such embodiments, the first second-electrode input may comprise a command to designate a position of the second electrode relative to the at least another electrode, e.g., the first electrode, of the plurality of electrodes. Additionally, the second second-electrode input may comprise a command to prevent the second electrode from being activated and the third second-electrode input may comprise a command to change a power setting corresponding to the second electrode.

The aforementioned GUI of a computer system may form a portion, or subsystem, or an ablation system. In addition to the GUI of the computer system, the ablation system may further comprise a catheter including an expandable balloon disposed thereon, the expandable balloon including a surface and the plurality of electrodes, including the first electrode and second electrode, disposed on the surface.

Accordingly, the GUI of the computer system may be used to facilitate control the catheter, including expanding the balloon and activating the electrodes, to perform an ablation procedure including at least the following steps: providing in a first sector of the display, a menu comprising a first dialog box, a second dialog box, and an ultimate dialog box; providing in a second sector of the display, an image of the expandable balloon comprising a plurality of electrode representations including a first-electrode representation; receiving at the processor a first first-dialog-box input from the first dialog box; changing an appearance of the first dialog box; changing an appearance of the second dialog box; receiving at the processor a first first-electrode input from the first-electrode representation; and changing the first-electrode representation.

The method may also include steps of changing the image of the balloon, changing the appearance of the second dialog box, simultaneously or sequentially changing the appearance of each of the plurality of electrode representations, activating at least one of the plurality of electrodes, displaying a measure of progress (e.g., a timer), displaying a global power, second changing the first-electrode representation, third changing the first-electrode representation, activating a pump to cause an irrigation fluid to expand the expandable balloon, designating the first electrode as being disposed posteriorly to at least another electrode of the plurality of electrodes (e.g., the first electrode), and changing a power setting corresponding to the first electrode.

Where the plurality of electrodes comprises a second electrode and the plurality of electrode representations comprises a second-electrode representation, further variations of the method may include steps of receiving at the processor a first second-electrode input and then changing the second-electrode representation before second changing and then third changing the second-electrode representation. In some further variations, the first second-electrode input may comprise a command to designate the second electrode as being disposed posteriorly to the least another electrode of the plurality of electrodes.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1:
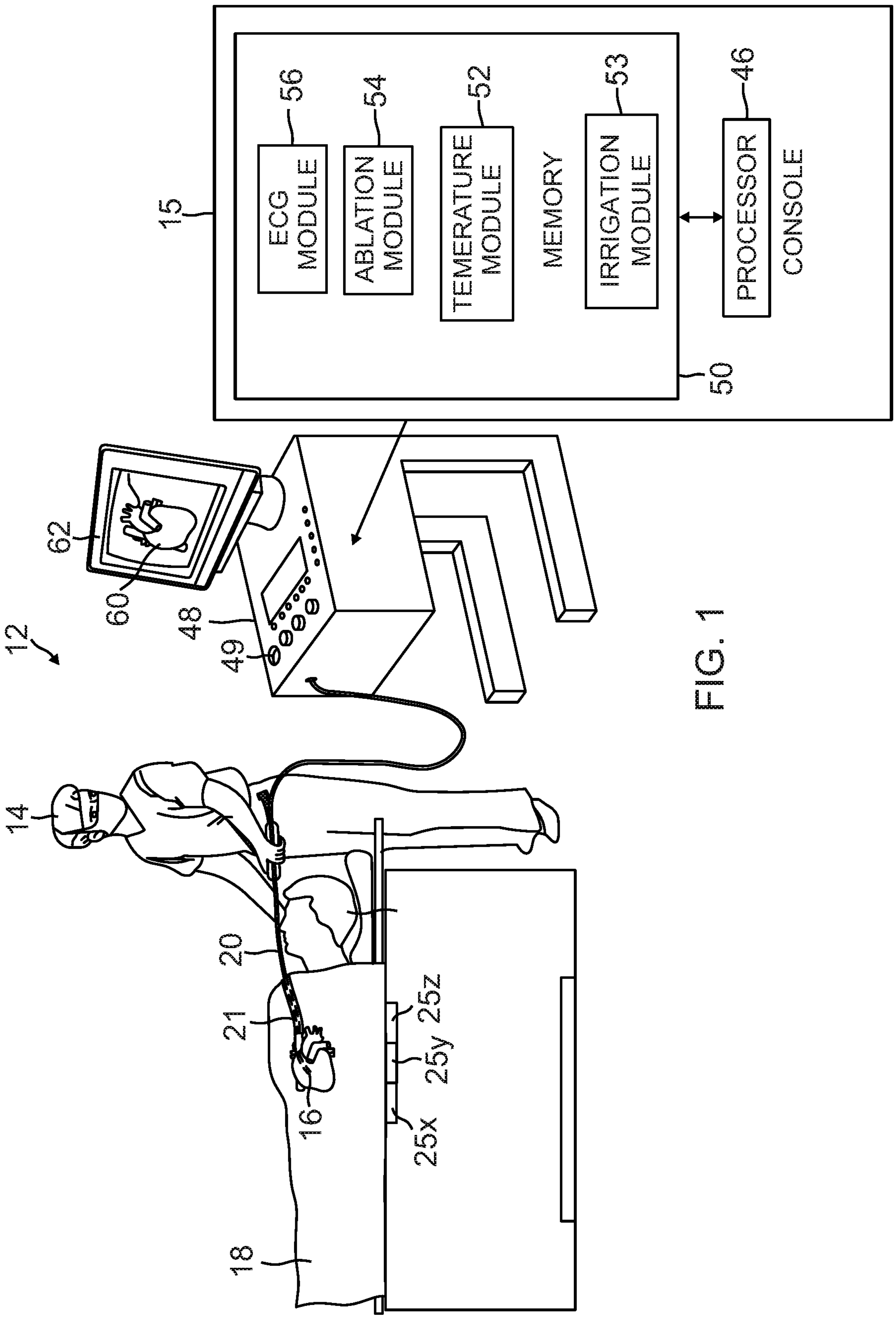
FIG. 1 is a schematic illustration of an invasive medical procedure.

FIG. 1 is a schematic illustration of an invasive medical procedure using apparatus 12, according to an embodiment. The procedure is performed by a medical professional 14, and, by way of example, the procedure in the description hereinbelow is assumed to comprise ablation of a portion of a myocardium 16 of the heart of a human patient 18. However, it is understood that embodiments disclosed herein are not merely applicable to this specific procedure, and may include substantially any procedure on biological tissue or on non-biological materials.

Figure 2:
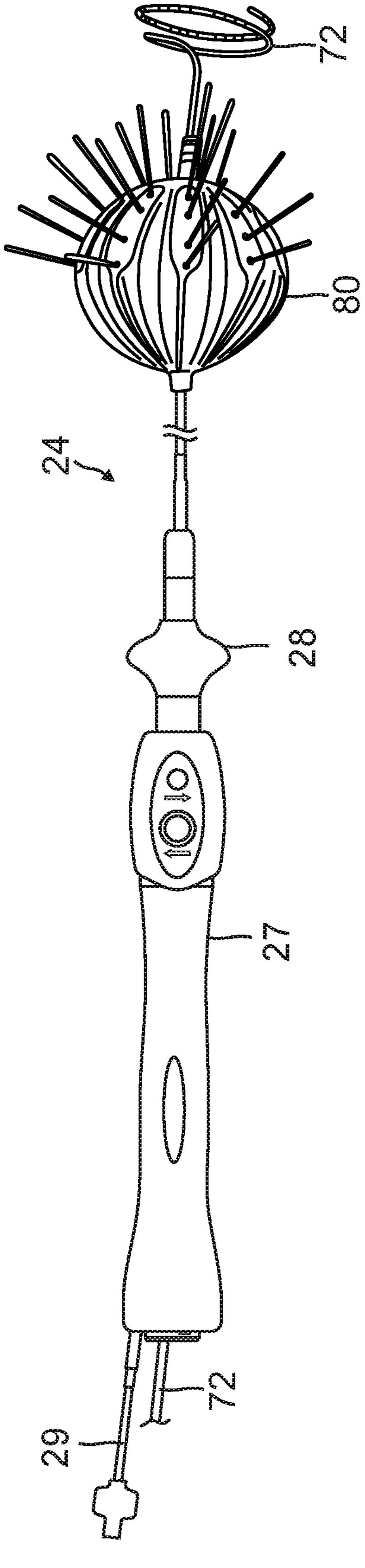
FIG. 2 is a top view of a catheter with a balloon in an expanded state, in use with a lasso catheter.

To perform the ablation, medical professional 14 inserts a probe 20 into a sheath 21 that has been pre-positioned in a lumen of the patient. Sheath 21 is positioned so that a distal end of probe 20 enters the heart of the patient. A diagnostic/therapeutic catheter 24 (e.g., a balloon catheter), which is described in more detail below with reference to FIG. 2, is deployed through a lumen of the probe 20, and exits from a distal end of the probe 20.

As shown in FIG. 1, apparatus 12 is controlled by a system processor 46, which is in an operating console 48 of the apparatus, also shown schematically at reference numeral 15. Console 48 comprises controls 49 and screen 62, which may be used by medical professional 14 to communicate with the processor As such, screen 62 may comprise a touch screen and controls 49 may comprise, e.g., a mouse or trackball. During the procedure, processor 46 typically tracks a location and an orientation of the distal end of the probe 20, using any method known in the art. For example, processor 46 may use a magnetic tracking method, wherein magnetic transmitters 25X, 25Y and 25Z external to the patient 18 generate signals in coils positioned in the distal end of the probe 20. The CARTO® system (available from Biosense Webster, Inc. of Irvine, California) uses such a tracking method.

The software for the processor 46 may be downloaded to the processor in electronic form, over a network, for example. Alternatively, or additionally, the software may be provided on non-transitory tangible media, such as optical, magnetic, or electronic storage media. The tracking of the distal end 22 may be displayed on a three-dimensional representation 60 of the heart of the patient 18 on screen 62. However, it may be displayed two-dimensionally, e.g., by fluoroscopy or MRI.

To operate apparatus 12, processor 46 communicates with a memory 50, which has many modules used by the processor to operate the apparatus. Thus, the memory 50 comprises a temperature module 52, an ablation module 54, and an electrocardiograph (ECG) module 56. The memory 50 typically comprises other modules, such as a force module for measuring the force on the distal end 22, a tracking module for operating the tracking method used by the processor 46, and an irrigation module 53 connected to a pump allowing the processor to control the pump, and thus irrigation provided to the catheter. For simplicity, such other modules are not illustrated in FIG. 1. The modules may comprise hardware as well as software elements. For example, module 54 may include a radio-frequency generator with at least one output or output channel, e.g., ten outputs or ten output channels. Each of the outputs may be separately and selectively activated or deactivated by a switch. That is, each switch may be disposed between the signal generator and a respective output. Thus, a generator with ten outputs would include ten switches. These outputs may each be individually coupled to electrodes on an ablation catheter, e.g., the ten electrodes 33 on balloon 80, described in further detail below. Such an electrical connection may be achieved by establishing an electrical path between each output and each electrode. For example, each output may be connected to a corresponding electrode by one or more wires or suitable electrical connectors. Thus, in some embodiments, an electrical path may include at least one wire. In some embodiments, the electrical path may further include an electrical connector and at least a second wire. Thus, electrodes 33 may be selectively activated and deactivated with the switches to receive radiofrequency energy separately from each of the other electrodes.

Figure 3:
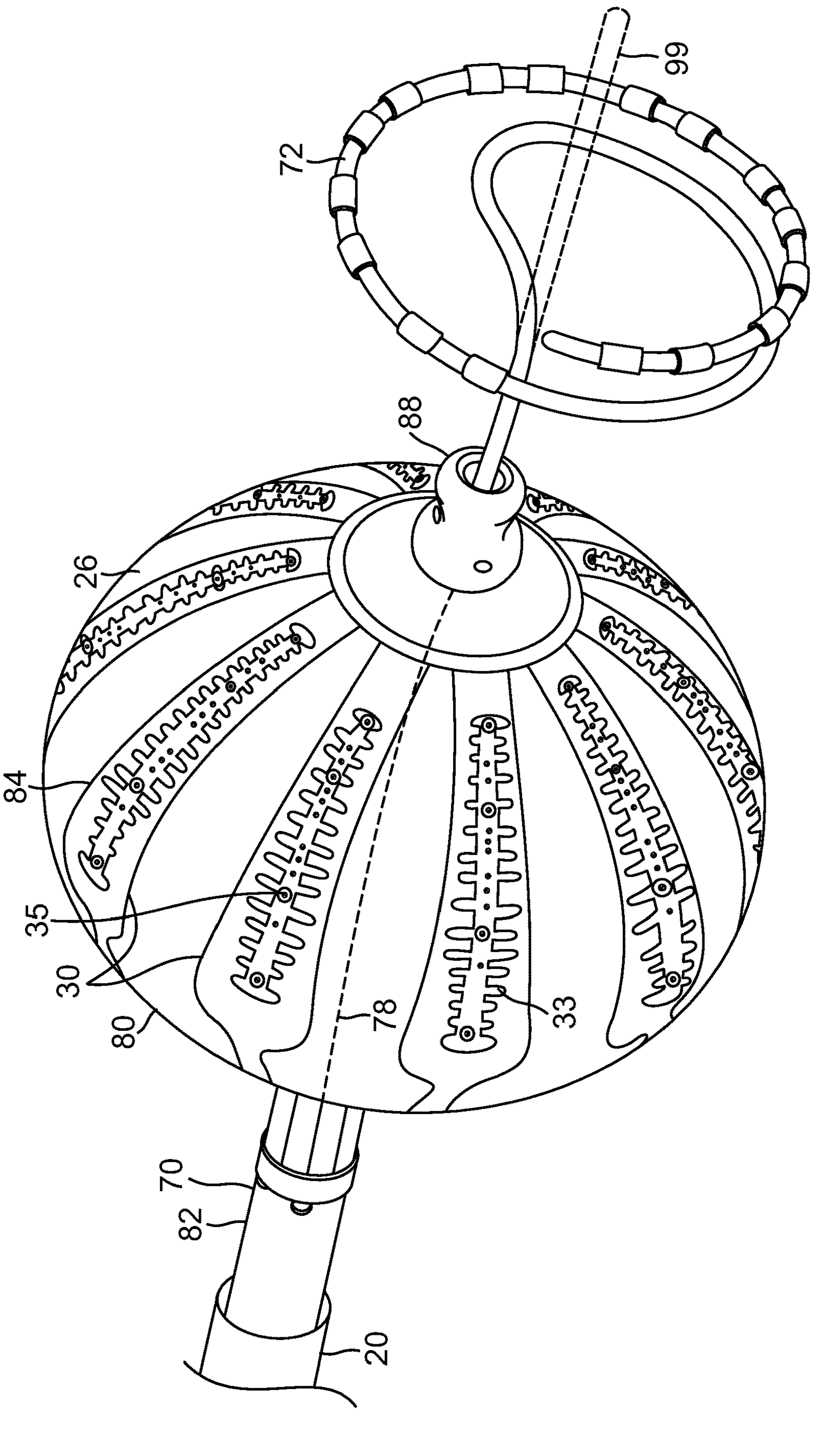
FIG. 3 is a perspective view of a balloon of FIG. 2, along with the lasso catheter.
Figure 4:
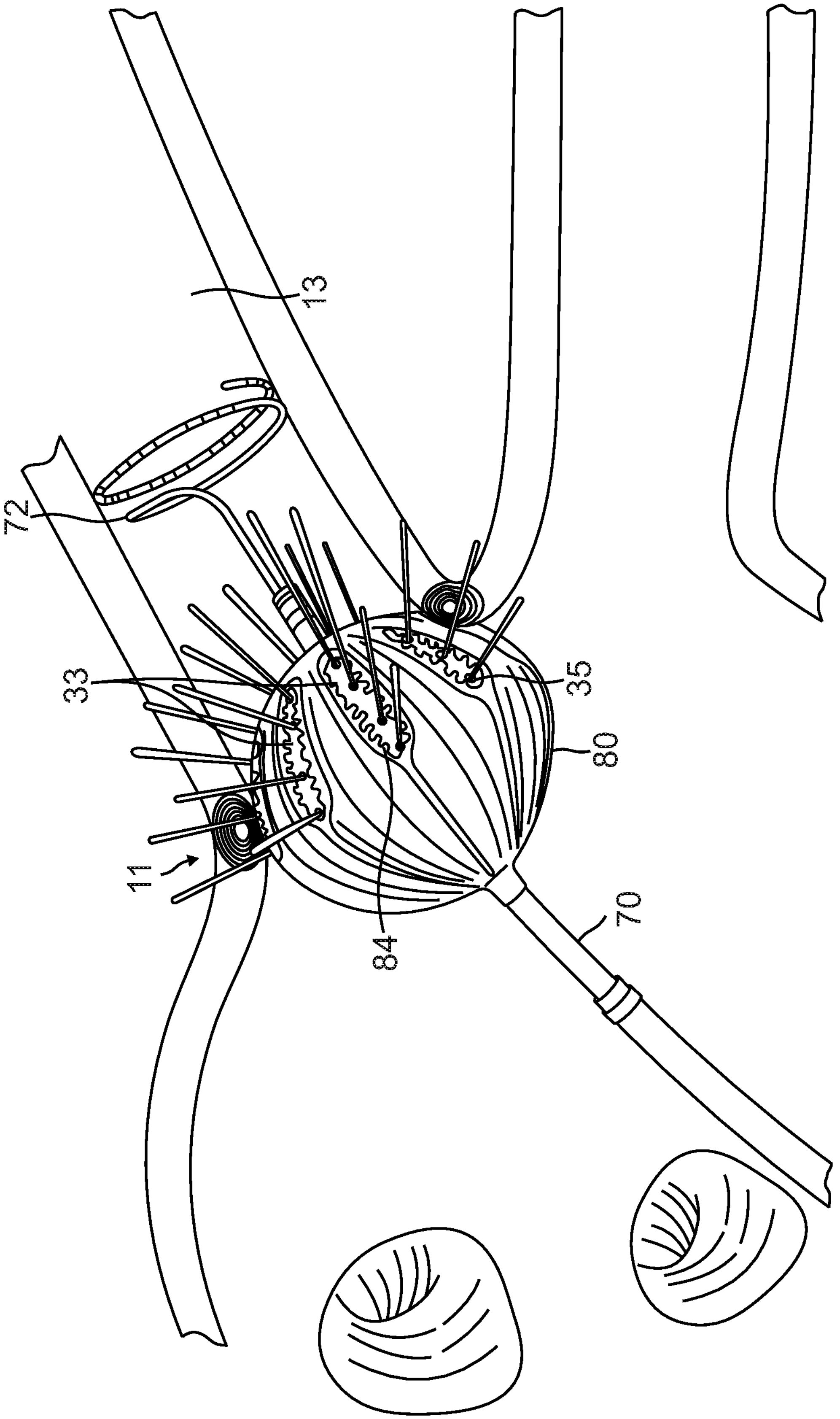
FIG. 4 is a side view of a distal end of the catheter of FIG. 2 deployed in the region of a pulmonary vein and its ostium.

FIG. 2 is a schematic perspective view of the diagnostic/therapeutic catheter 24 in in which balloon 80 is in an expanded configuration. Catheter 24 may include a handle 27, a plunger 28, and irrigation tubing 29. Plunger 28 may be used to open and close an irrigation lumen that passes through catheter 24 and connects tubing 29 to balloon 80, such that an irrigation fluid (e.g., saline) may be introduced or pumped through tubing 29 and ultimately into balloon 80 by a pump connected to a source of the irrigation fluid and irrigation module 53. Specifically, plunger 28 may be pulled proximally toward handle 27 to open the irrigation lumen and pushed distally away from handle 27 to close the irrigation lumen. With further reference to FIGS. 3 and 4, where the diagnostic/therapeutic catheter 24 is used to ablate an ostium 11 of a lumen, such as a pulmonary vein 13, the diagnostic/therapeutic catheter 24 may be supported by a tubular shaft 70 having a proximal shaft portion 82 and a distal shaft end 88. The shaft 70 includes a hollow central tube 74, which permits another catheter to pass therethrough and past the distal shaft end 88, such as a lasso catheter 72. The lasso catheter 72 may be inserted into the pulmonary vein to position the diagnostic/therapeutic catheter 24 correctly with respect to the ostium prior to ablation of the ostium. The distal lasso portion of catheter 72 is typically formed of shape-memory retentive material such as nitinol. It is understood that the diagnostic/therapeutic catheter 24 may also be used with a linear or focal catheter 99 (as shown in broken lines in FIG. 3) in the PV or elsewhere in the heart. The focal catheter 99 may include a force sensor at its distal tip. Suitable force sending distal tips are disclosed in U.S. Pat. No. 8,357,152, issued on Jan. 22, 2013 to Govari et al., titled CATHETER WITH PRESSURE SENSING, and in U.S. Patent Application 2011/0130648, to Beeckler et al., filed Nov. 30, 2009, titled CATHETER WITH PRESSURE MEASURING TIP, the entire contents of both of which are incorporated herein by reference. Any catheter used in conjunction with the diagnostic/therapeutic catheter may have features and functions, including, for example, pressure sensing, ablation, diagnostic, e.g., navigation and pacing.

The balloon 80 of the diagnostic/therapeutic catheter 24 has an exterior wall, surface, or membrane 26 of a biocompatible material, for example, formed from a plastic such as polyethylene terephthalate (PET), polyurethane or PEBAX®. The shaft 70 and the distal shaft end 88 define a longitudinal axis 78 of the balloon 80. The balloon 80 is deployed, in a collapsed configuration, via the lumen 23 of the probe 20, and may be expanded after exiting from the distal end. The membrane 26 of the balloon 80 may be formed with irrigation pores or apertures 35 through which fluid (e.g., saline) can exit from the interior of the balloon 80 to outside the balloon for cooling the tissue ablation site at the ostium. While FIG. 2 and FIG. 4 show fluid exiting the balloon 80 as jet streams, the fluid may exit the balloon with any desired flow rate or pressure, including a rate where the fluid is seeping out of the balloon.

The membrane 26 supports and carries combined electrode and temperature sensing members which are each constructed as a multi-layer flexible circuit electrode assembly 84. The "flex circuit electrode assembly" 84 may have many different geometric configurations. In the illustrated embodiment, the flex circuit electrode assembly 84 has a plurality of radiating substrates or strips 30 upon which are disposed electrodes 33. The substrates 30 are evenly distributed about the distal end 88 and the balloon 80. Each substrate has wider proximal portion that gradually tapers to a narrower distal portion.

Screen 62 or an additional iteration thereof, may be used to display one or more displays of a graphical user interface (GUI), which may assist medical professional 14 to communicate with processor 46 and receive information therefrom to conduct an ablation procedure using diagnostic/therapeutic catheter 24. Representations of exemplary displays of the GUI are reflected in FIGS. 5-18. Medical professional 14 may provide certain inputs to processor 46 via the various GUI displays. The various GUI displays may also be used to guide medical professional 14 through the procedure by providing, e.g., recommendations, notifications, and alerts. Accordingly, each display may correspond to a distinct step or segment of the ablation procedure. As such, the GUI displays may be configured to permit medical professional 14 to make inputs to processor 46 relevant to the step or segment of the ablation procedure corresponding to a given screen, while preventing medical professional 14 from making inputs to processor 46 that are not relevant to the step or segment of the ablation procedure. Furthermore, based on determinations made by processor 46, processor 46 may modify the displays to communicate that certain inputs may no longer be provided by medical professional 14 to processor 46.

Figure 5:
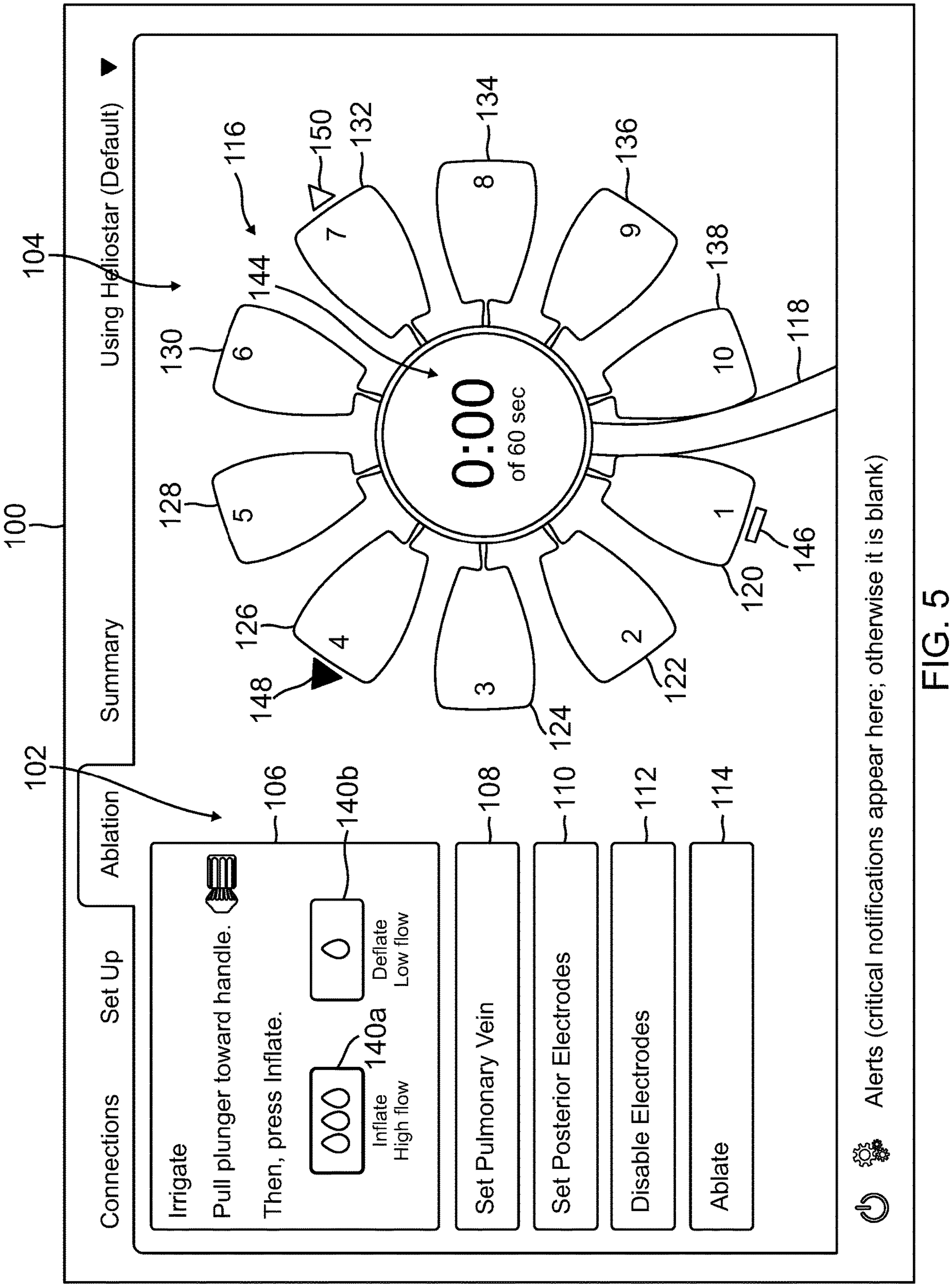
FIG. 5 is a first representation of a graphical user interface (GUI) display.

A first exemplary representation of a GUI display 100 is reflected in FIG. 5. Display 100 may include a first sector 102 and second sector 104. First sector 102 and second sector 104 may be used to show different information corresponding to a procedure. For example, as shown, first sector 102 may include a menu comprising a plurality of dialog boxes, such as dialog box 106, dialog box 108, dialog box 110, dialog box 112, and dialog box 114. Further, dialog box 106 is shown in an expanded configuration whereas dialog boxes 108, 110, 112, and 114 are shown in a collapsed configuration. These dialog boxes each correspond to distinct steps or segments of an ablation procedure. As seen in FIG. 5, for example, the first segment of the procedure is related in dialog box 106. Hence during the first segment of the procedure, dialog box 106 is expanded whereas the remainder are collapsed, thus preventing professional 14 from providing inputs to processor 46 unrelated to expanding balloon 80. In this segment of the procedure, an irrigation fluid, e.g., saline, may be provided through catheter 24 and into balloon 80, which assists balloon 80 to expand. Dialog box 106 thus provides instructions, e.g., text and graphical, concerning this segment of the procedure. As shown, dialog box 106 instructs to, e.g., "Pull plunger toward handle" and shows an image of the plunger, which may be a feature of catheter 24. Further, dialog box 106 includes icons 140*a* and 140*b* with which medical professional 14 may interact to provide commands relating to this segment to processor 46. For example, professional 14 may commence this segment of the procedure by communicating a start command to processor 46 by touching or clicking icon 140, thus causing a flow of the irrigation fluid having a volume flow rate sufficient to expand balloon 80. Further, because it may be necessary for professional 14 to collapse balloon 80, e.g., for repositioning it, icon 140*b* may be used to instruct processor 46 to slow the flow of the irrigation fluid, which assists in collapsing the balloon.

Second sector 104 may include a graphical representation 116 of catheter 24, which may include representations or icons of balloon 80, such as electrodes 33 with or without a surface of balloon 80. As seen in FIG. 5, a catheter body of catheter 24 is reflected as catheter body 118 and electrodes 33, numbered 1-10, are reflected as icons 120, 122, 124, 126, 128, 130, 132, 134, 136, and 138. In representation 116 of balloon 80, membrane 26 of balloon 80 is not shown because balloon 80 has not yet been expanded. However in subsequent displays shown in subsequent figures corresponding to segments of the ablation process where balloon 80 has been expanded, a representation of membrane 26 may be reflected. For example, in FIG. 6, membrane 26 is represented by reference numeral 242. A center portion 144 may provide information about the ablation procedure, e.g., a timer indicating the elapsed time since ablation energy began to be provided to the electrodes. As such, in FIG. 5, which corresponds to a segment of the ablation procedure before ablation energy has been provided, the timer reflects "0:00." Further, balloon representation 116 may include icons, e.g., hollow rectangle 146, solid triangle 148, and hollow triangle 150, corresponding to markers, e.g., radiopaque markers as described in U.S. patent application Ser. No. 15/939,154, that may be disposed on various electrodes 33. Accordingly, these marker icons are positioned on or adjacent to the electrode representation having a corresponding marker. For example, where first electrode 33 (electrode 1) of balloon 80 includes a radiopaque marker having a hollow rectangular form, then icon 146 is disposed adjacent to first electrode icon 120.

Figure 6:
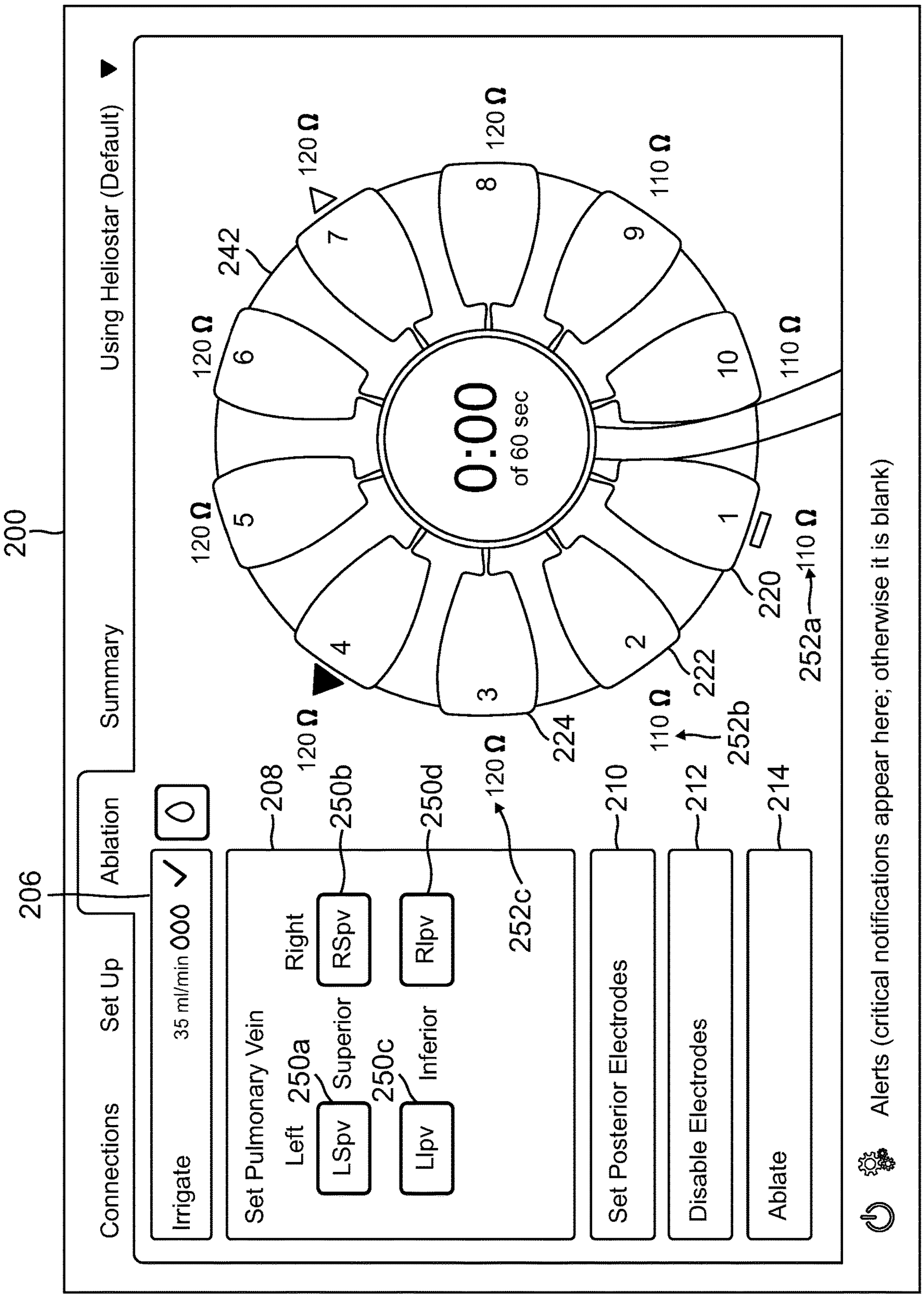
FIG. 6 is a second representation of a GUI display.

A second exemplary representation of a GUI display 200 is reflected in FIG. 6. GUI display 200 is similar to GUI display 100 except for the differences described herein. Further, in this example, GUI display 200 corresponds to a segment of the ablation process subsequent to the segment of the ablation process corresponding to GUI display 100. Specifically, GUI display 200 corresponds to a segment in which professional 14 determines the pulmonary vein in which balloon 80 has been or is to be disposed, and then informs processor 46 of this using information and icons in now expanded dialog box 208. Dialog boxes 206, 210, 212, and 214 are collapsed to prevent instructions from being provided relating to other segments of the process. As shown, dialog box 206 includes four icons 250*a*, 250*b*, 250*c*, and 250*d*, labeled as LSpv, RSpv, LIpv, and RIpv, i.e., abbreviations for Left Superior Pulmonary Vein, Right Superior Pulmonary Vein, Left Inferior Pulmonary Vein, and Right Inferior Pulmonary Vein. Professional 14 may communicate to processor 46 the pulmonary vein in which balloon 80 will be disposed.

The representation of balloon 80 in display 200 now includes a representation 242 of membrane 26 because, in the version of the ablation procedure described herein, balloon 80 has been expanded. Further, indications of physical or electrical quantities, e.g., current or impedance, associated with one or more electrodes 33 may be provided alongside the corresponding electrode icons. As shown in FIG. 6, impedance indications are provided adjacent to electrode icons, e.g., impedance indications 150*a, b*, and *c* alongside icons 220, 222, and 224. For example, the impedance indications may inform professional 14 of the maximum impedance that processor 46 will allow to each electrode 33 such that if the maximum impedance is surpassed, processor 46 may deactivate the electrode.

Figure 7:
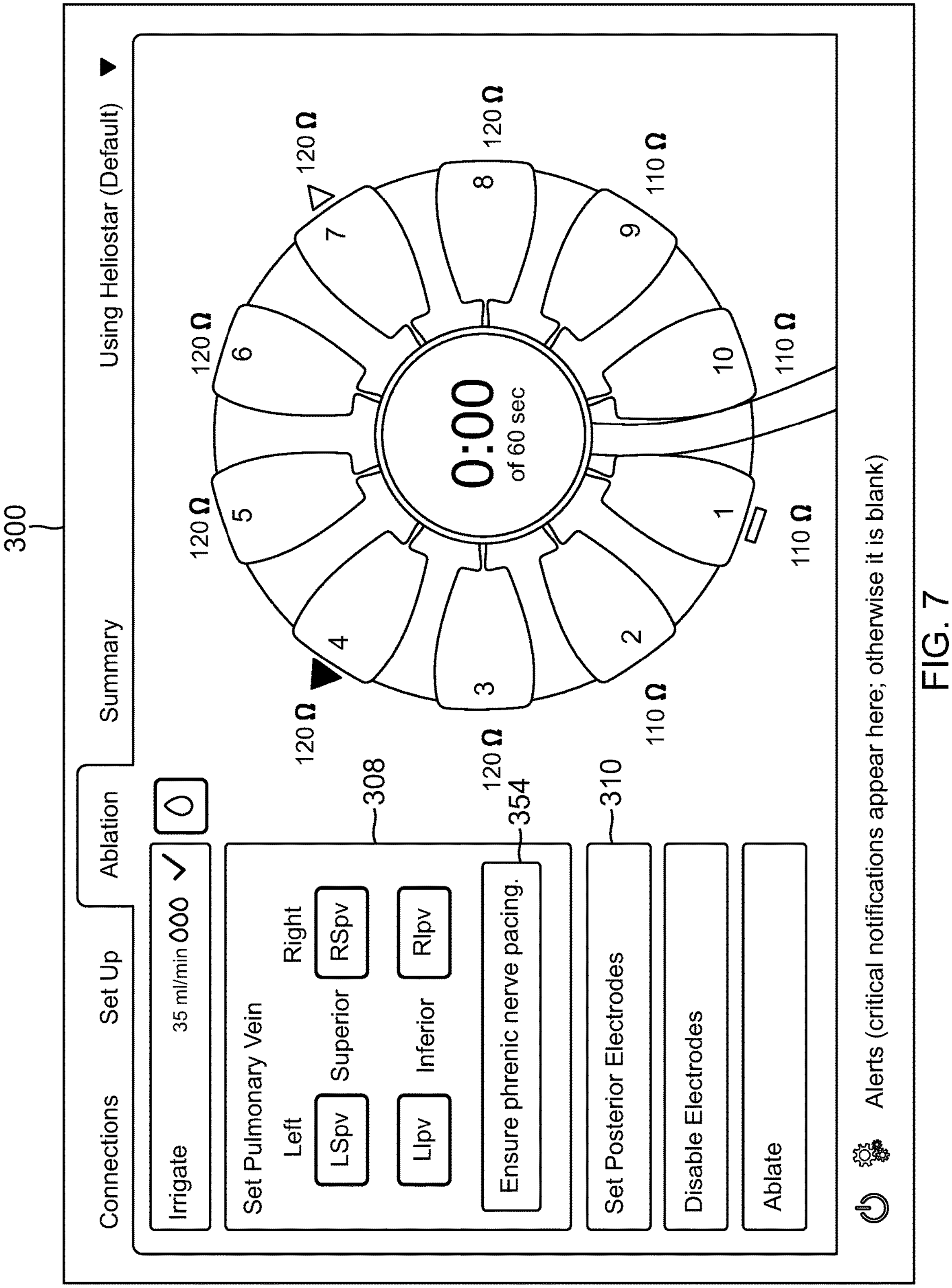
FIG. 7 is a third representation of a GUI display.

A third exemplary representation of a GUI display 300 is reflected in FIG. 7. GUI display 300 is similar to GUI display 200 except for the differences described herein. Further, in this example, GUI display 300 corresponds to a step of the ablation process subsequent to the steps described for GUI display 200. After the pulmonary vein is selected by professional 14, dialog box 308 may provide a message, e.g., via confirmation icon or box 354, to professional 14. For example, it may be useful to remind professional 14 to ensure that phrenic nerve pacing has been enabled, e.g., via a pacing system, such that a patient will continue to breathe properly during the ablation segment of the ablation procedure. Further, processor 46 may require receipt of an input corresponding to professional 14 touching or clicking icon 354 before processor 46 will advance GUI display 300 to a subsequent GUI display.

Figure 8:
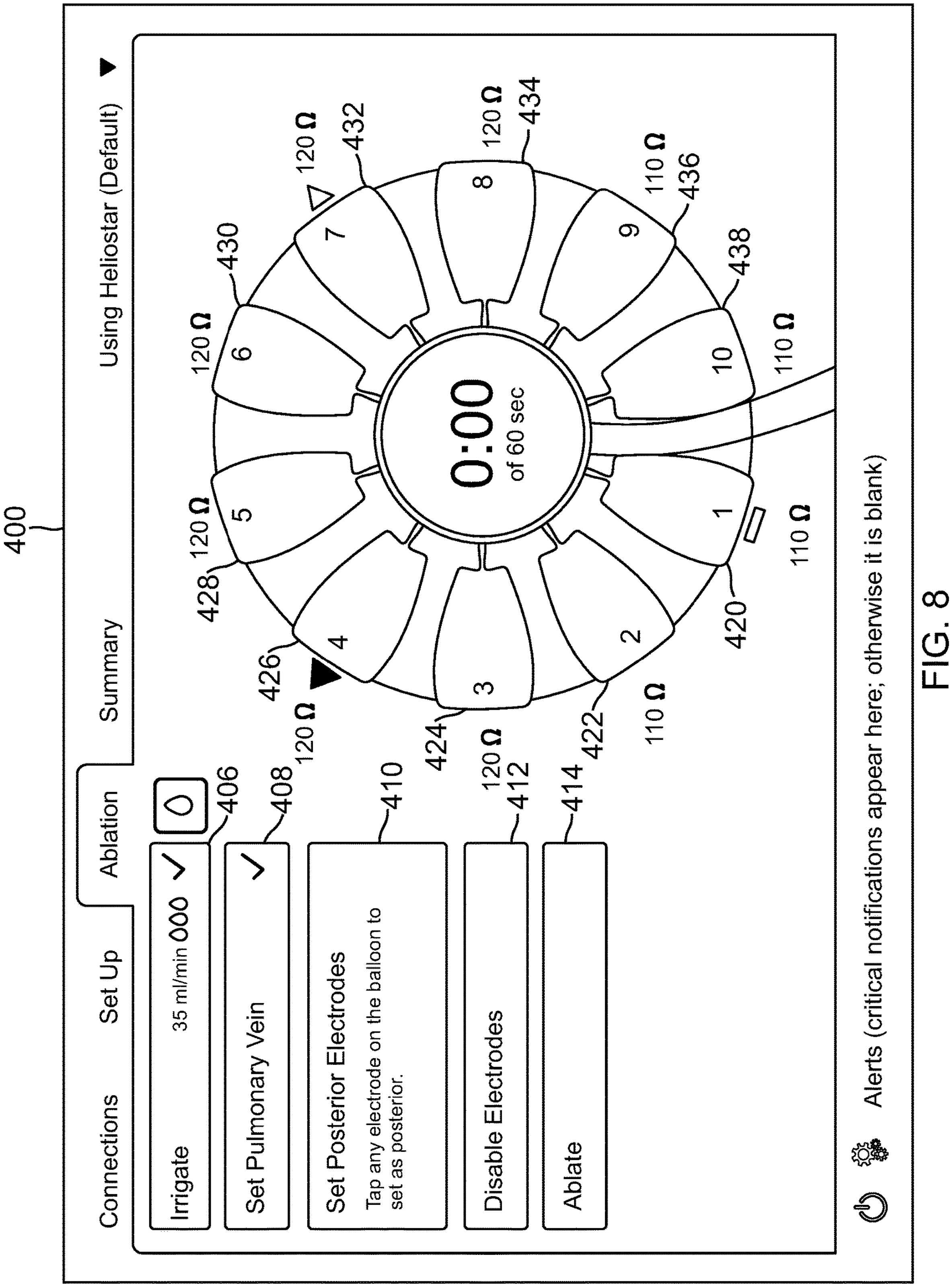
FIG. 8 is a fourth representation of a GUI display.

A fourth exemplary representation of a GUI display 400 is reflected in FIG. 8. GUI display 400 is similar to GUI display 300 except for the differences described herein. Further, in this example, GUI display 400 corresponds to a segment of the ablation process subsequent to the step described for GUI display 300. Specifically, GUI display 400 corresponds to a segment of the ablation process in which professional 14 determines which electrodes 33 are positioned toward the posterior of a patient relative to the other electrodes 33. Based on this determination, professional 14 may touch or click the corresponding electrode icons from among electrode icons 420, 422, 424, 426, 428, 430, 432, 434, 436, and 438 to inform processor 46 of the determination. Such a determination may be useful during those segments of the procedure during which electrical current is provided to electrodes 33 because the posterior of the pulmonary veins, and thus the electrodes disposed thereby, are located proximate to the esophagus, such that safety considerations arising from this anatomy should be considered. Accordingly, in display 400, dialog box 408 may appear expanded whereas dialog boxes 406, 408, 412, and 414 appear collapsed. Further, dialog box 408 may instruct professional 14 to indicate her determinations of electrode positions by clicking or touching the posterior electrodes 33. Correspondingly, electrode icons 420, 422, 424, 426, 428, 430, 432, 434, 436, and 438 may have a different appearance on display 400 than in displays 100, 200, and 300. For example, because inputs to processor 46 corresponding to electrodes 33 were not relevant in the steps or segments of the ablation procedure corresponding to displays 100, 200, and 300, the electrode icons could be shown in gray, whereas on display 400, they may be shown in white, or flashing between white and gray, thus drawing the attention of professional 14 thereto as though requesting the input from professional 14.

Figure 9:
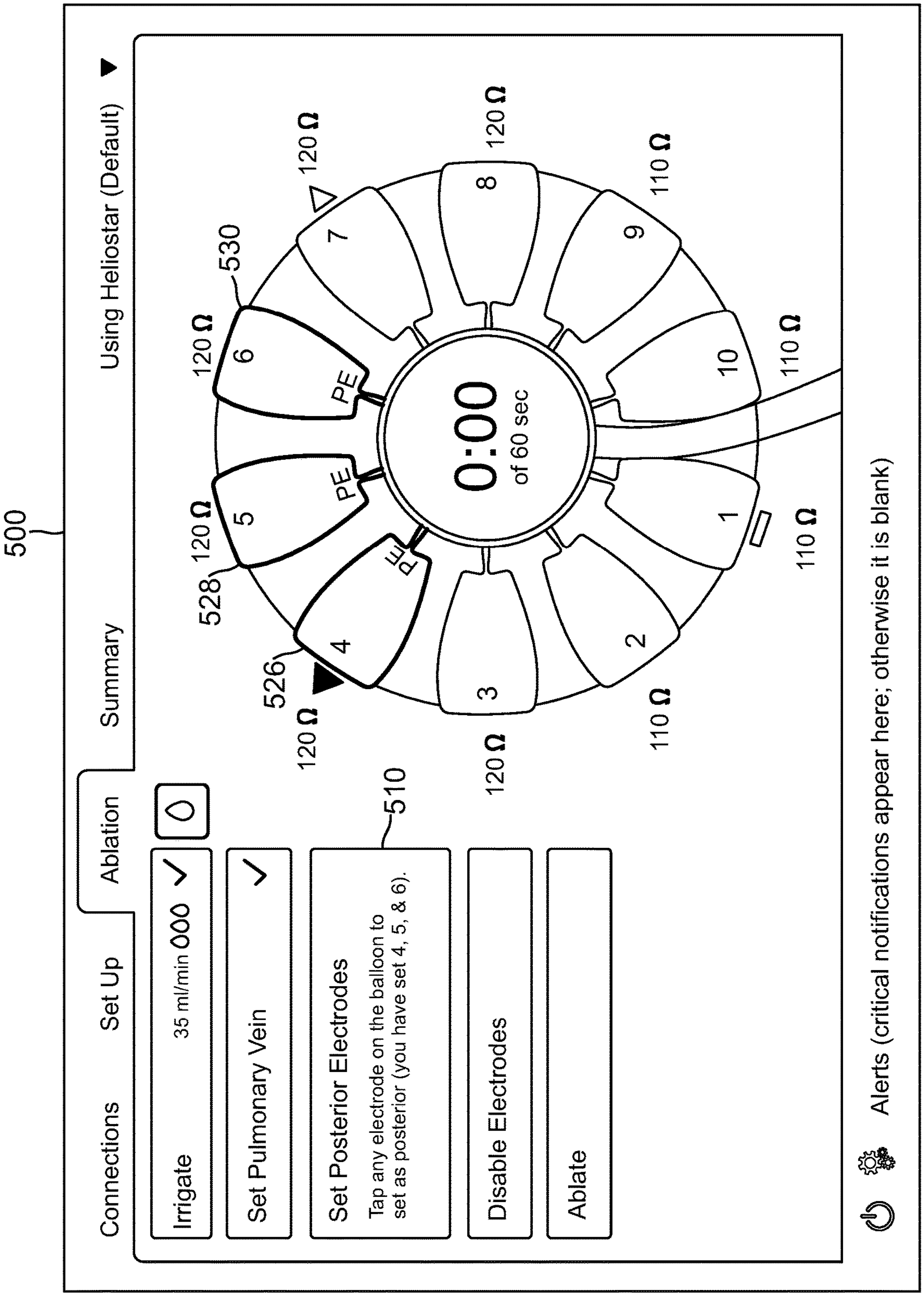
FIG. 9 is a fifth representation of a GUI display.

A fifth exemplary representation of a GUI display 500 is reflected in FIG. 9. GUI display 500 is similar to GUI display 400 except for the differences described herein. Further, in this example, GUI display 500 corresponds to a step of the ablation process subsequent to the steps described for GUI display 400. Specifically, as shown, electrode icons 526, 528, and 530 appear differently than did icons 426, 428, and 430 in display 400, reflecting that three electrodes 33 (electrodes 4-6) were identified to processor 46 as being located toward the posterior of the patient. As shown, electrode icons 526, 528, and 530 have a heavier contour than the other electrode icon. The heavier contour may be provided in a color or shade to readily distinguish these electrode icons from other electrode icons. Further the acronym "PE," which stands for Posterior Electrode, may also be provided on icons 526, 528, and 530. Additionally, or alternatively, the overall color of the icons 526, 528, and 530, and not just the color of the contours, may be changed relative to the other electrode icons. Further, dialog box 510 may be updated relative to dialog box 410 to indicate the selected electrodes. These indications may be used to make apparent and remind professional 14 of her determination concerning the relative positions of electrodes 33.

Figure 10:
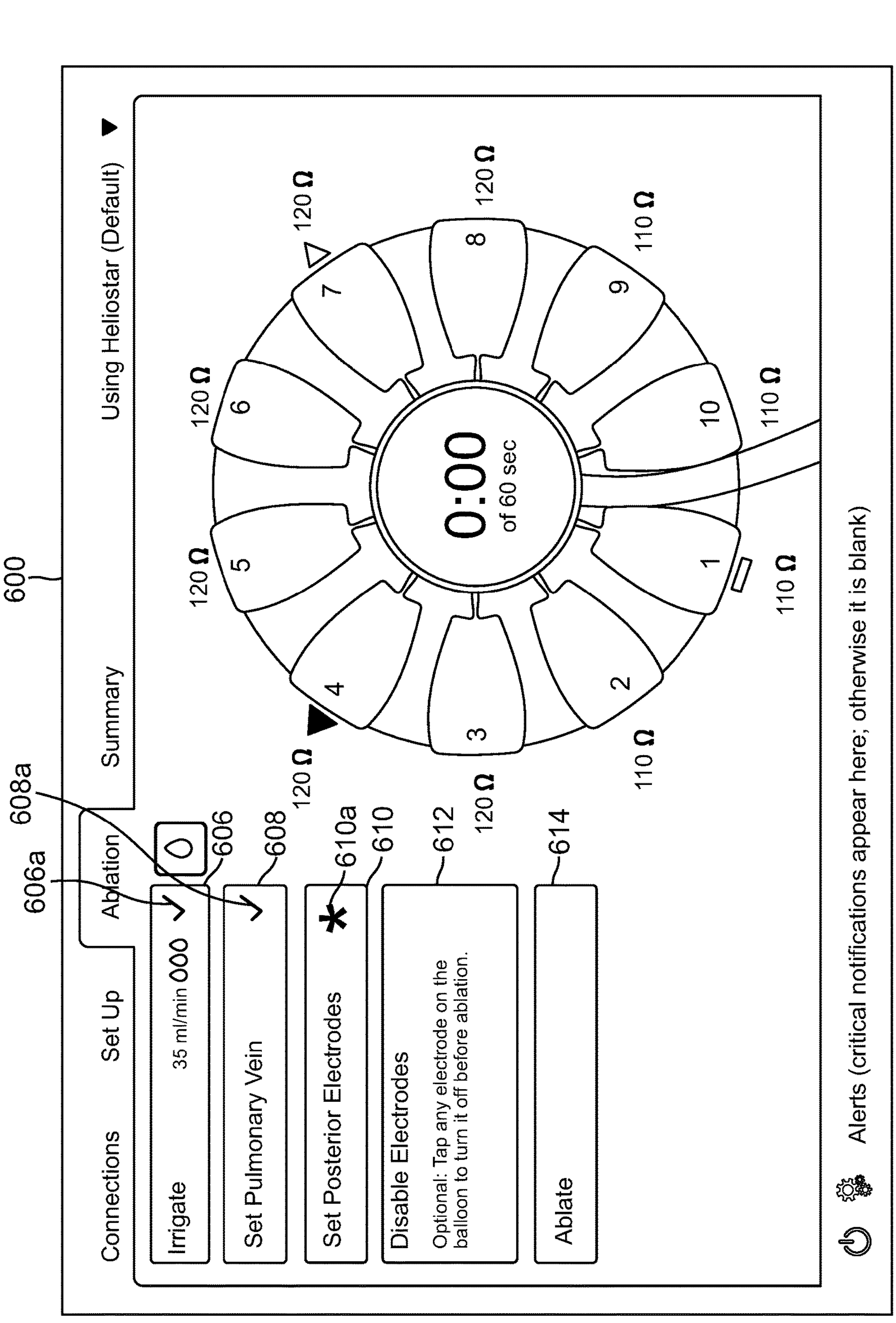
FIG. 10 is a sixth representation of a GUI display.

A sixth exemplary GUI display 600 is reflected in FIG. 10. GUI display 600 is similar to GUI display 400 except for the differences described herein. Further, in this example, GUI display 600 corresponds to a step of the ablation process subsequent to the steps described for GUI display 400. GUI display 600 reflects a decision by professional 14 to not identify to processor 46 any posterior electrodes. As such, instead of reflecting a changed appearance to corresponding electrode icons (e.g., 526, 528, 530), GUI display 600 may provide an alert that no posterior electrodes were selected. For example, an asterisk 610*a* may be placed in dialog box 610 instead of a check mark, such as check mark 606*a* in dialog box 606 and checkmark 608*a* in dialog box 608.

Additionally, GUI Display 600 corresponds to a step of an ablation procedure whereby professional 14 determines if any electrodes 33 should not be activated, i.e., receive any electrical current, for ablating tissue, and then communicates this decision to processor 46. Inasmuch as professional 14 may determine that all electrodes should be activated, the step of disabling electrodes, or informing processor 46 thereof via Display 600, may be considered optional. Such may be reflected in an instruction inside dialog box 612, which appears expanded on display 600, whereas dialog boxes 606, 608, 610, and 614 are shown collapsed.

Figure 11:
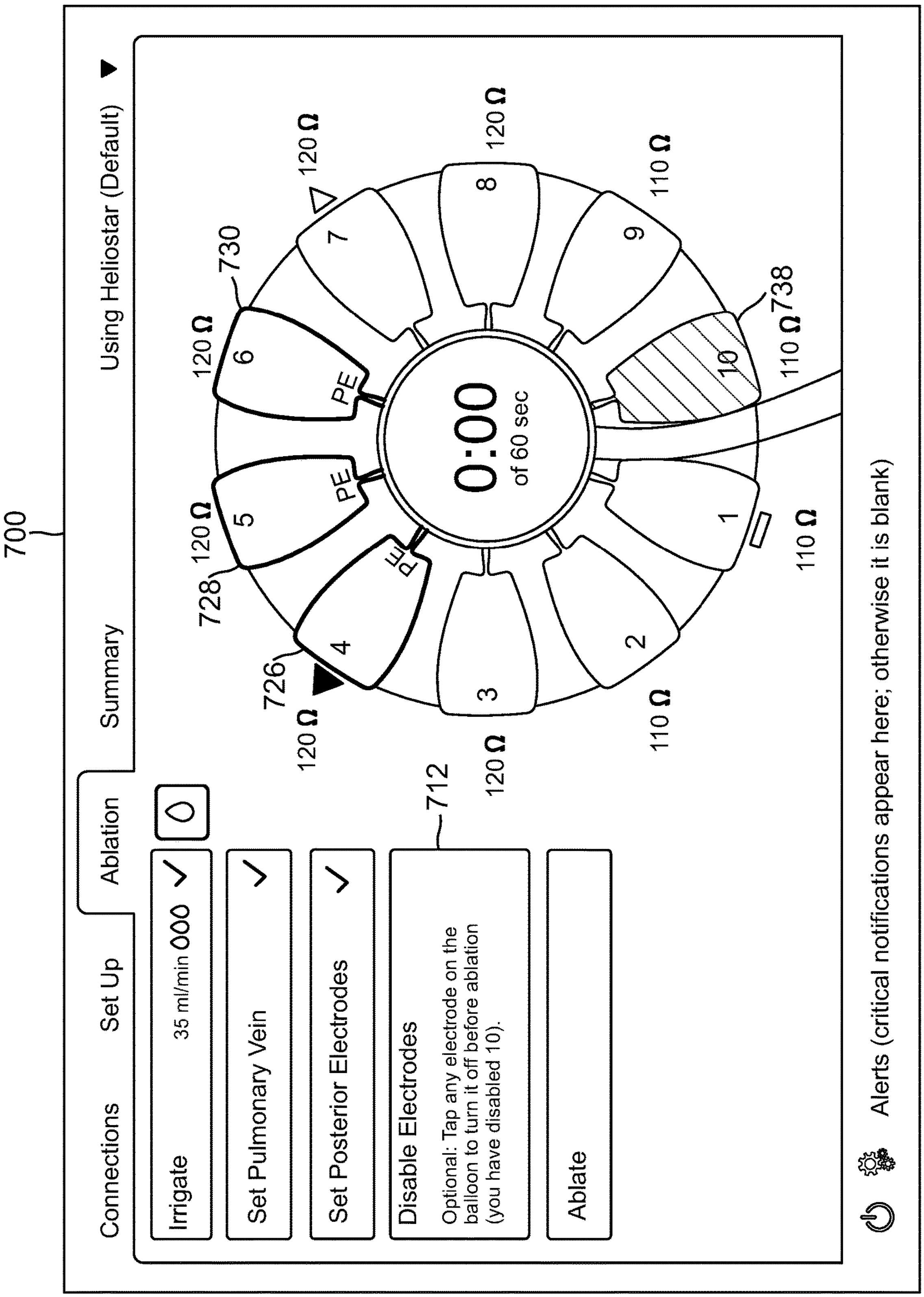
FIG. 11 is a seventh representation of a GUI display.

A seventh exemplary GUI display 700 is reflected in FIG. 11. GUI display 700 is similar to GUI display 600 except for the differences described herein. GUI display 700 reflects that professional 14 determined that the tenth electrode 33 should be disabled and communicated this decision to processor 46 by touching or clicking on electrode icon 738. As such, the appearance of electrode icon 738 has been changed relative to the appearance of the other electrode icons. Additionally or alternatively, a note may be provided in dialog box 712 indicating that the tenth electrode has been disabled. GUI display 700 also reflects that various electrodes 33 (i.e., electrodes 4-6), corresponding to electrode icons 726, 728, and 730, were identified to processor 46 as being posterior electrodes, similar to GUI display 500.

Figure 12:
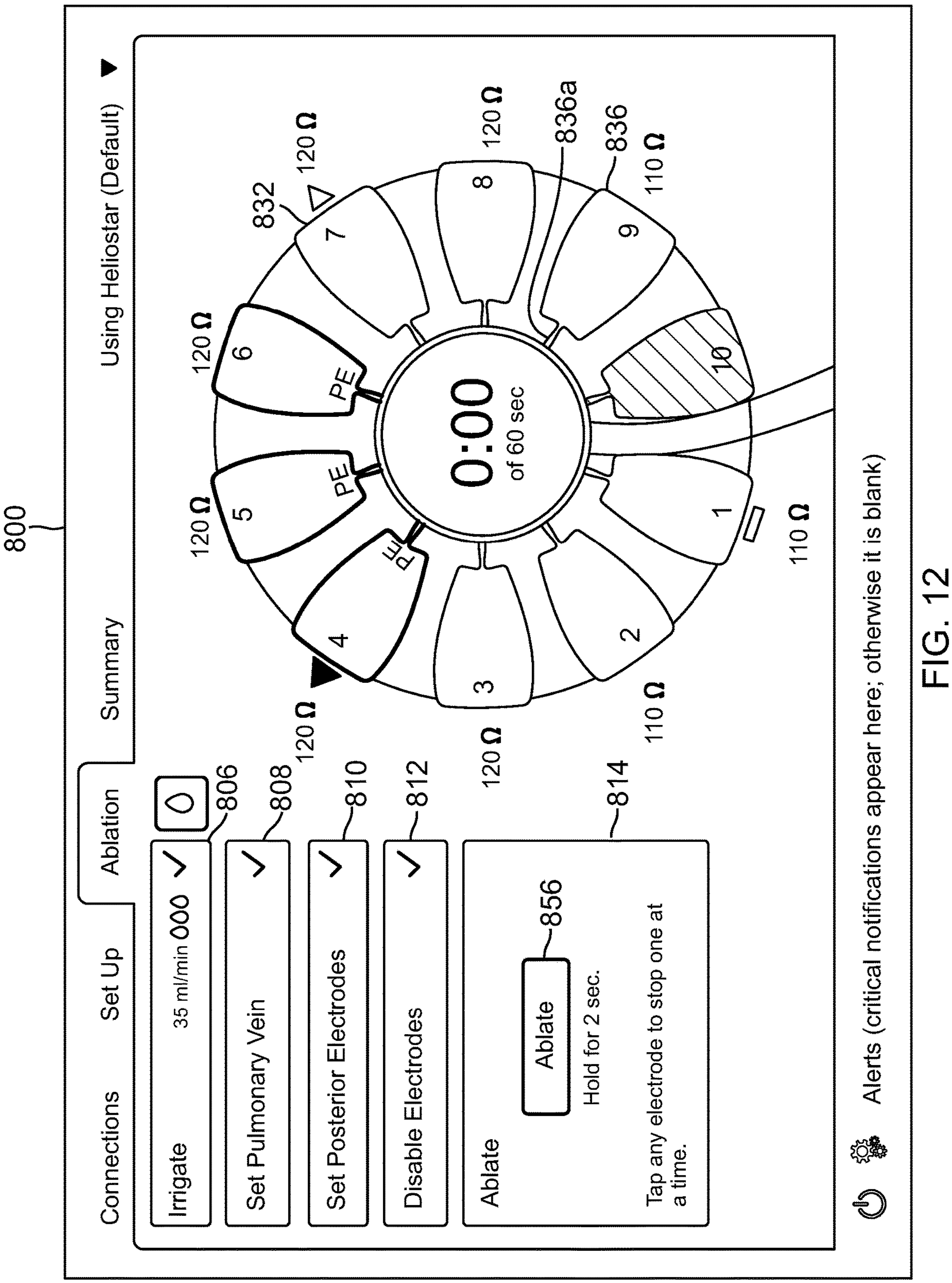
FIG. 12 is an eighth representation of a GUI display.

An eighth exemplary GUI display 800 is reflected in FIG. 12. GUI display 800 is similar to GUI display 700 except for the differences described herein. Further, in this example, GUI display 800 corresponds to a step of the ablation process subsequent to the steps described for GUI display 700. Specifically, GUI display 800 corresponds to a segment of the ablation procedure in which tissue ablation may be commenced. Display 800 is configured to invite an instruction from professional 14 to processor 46 to commence tissue ablation, which would cause processor 46 to activate any electrodes 33 that were not disabled previously. Accordingly, dialog box 814 is shown in an expanded configuration whereas dialog boxes 806, 808, 810, and 812 are collapsed. Dialog box 814 includes a box 856 therein that a surgeon may touch or click to activate electrodes 33. To ensure purposeful activation by professional 14, processor 46 may be configured to require that professional 14 touches or clicks on box 856 for a duration of time, such as about one to five seconds, e.g., about two seconds. Dialog box 814 may thus provide a written instruction of any such requirement.

Figure 13:
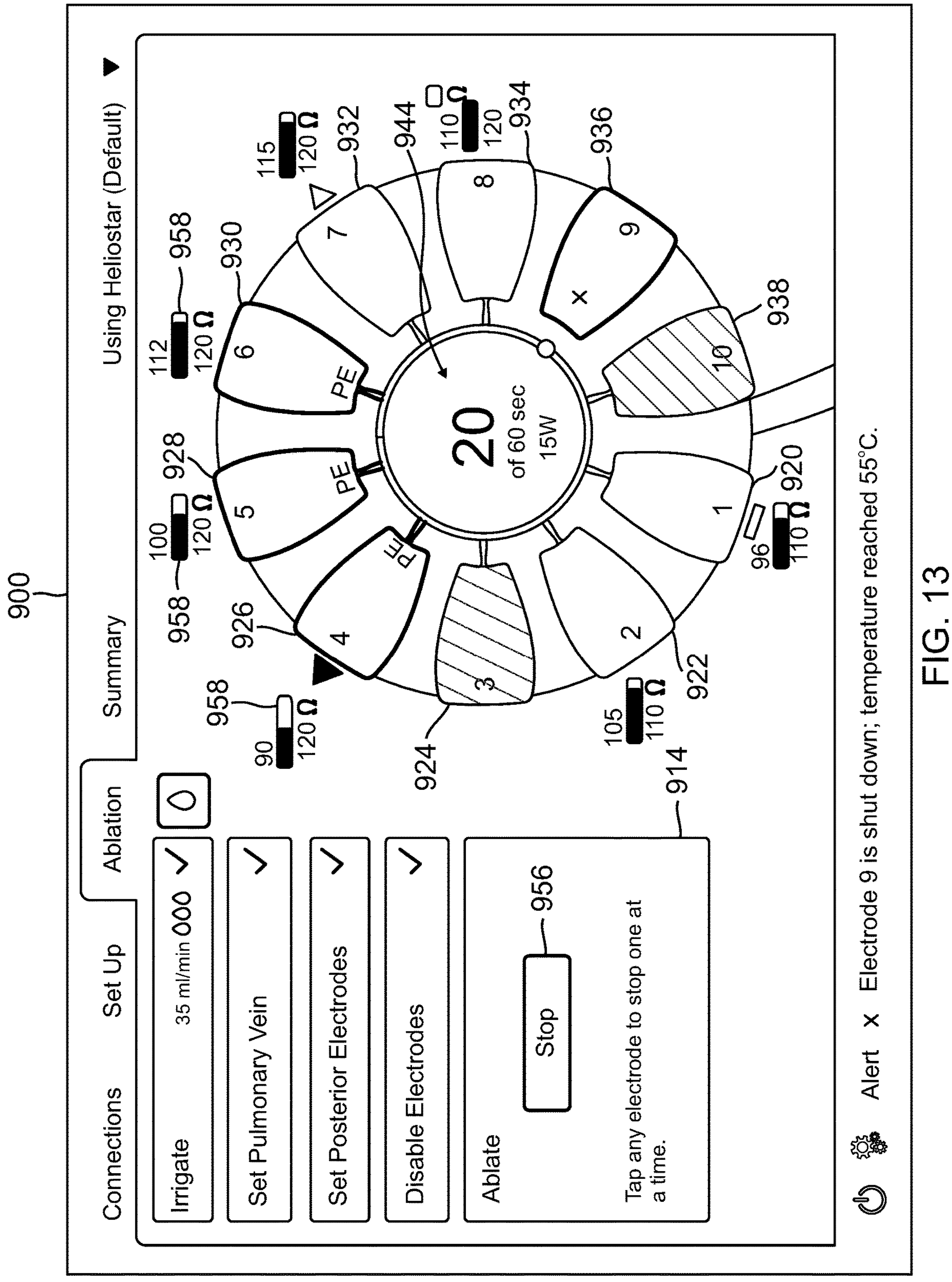
FIG. 13 is a ninth representation of a GUI display.

A ninth exemplary GUI display 900 is reflected in FIG. 13. GUI display 900 is similar to GUI display 800 except for the differences described herein. Further, in this example, GUI display 900 corresponds to a step of the ablation process subsequent to the steps described for GUI display 800. Specifically, GUI display 900 corresponds to a segment of the ablation process during which at least some of electrodes 33 have been activated. As seen in center portion 944, it appears that twenty seconds have elapsed and that power is being supplied to the active electrodes at 15 watts. Dialog box 914 remains in an expanded configuration, however, box 956 is now configured to accept an input from professional 14 to deactivate all active electrodes 33. Further, dialog box 914 provides an instruction that any individual electrode 33 may be deactivated by tapping the corresponding electrode icon. As shown, display 900 reflects that such was done for the third electrode corresponding to electrode icon 924 as indicated by the hatching.

Display 900 may also reflects certain electrodes 33 that may be disabled by processor 46, e.g., upon a determination that the temperatures of those electrodes may exceed a safety maximum. As shown, the ninth electrode corresponding to electrode icon 936 has been disabled by processor 46. Such may be indicated in various ways, e.g., by thickening the contour of the electrode icon, changing its color, adding a mark (e.g., an "x"), removing the icon's connection to center portion 944—note reference numeral 836*a* on display 800, FIG. 12. A corresponding alert may be provided on display 900, e.g., at the bottom thereof as shown.

All electrodes 33 that are active, e.g., electrodes corresponding to electrode icons 920, 922, 926, 928, 930, 932, and 934 on Display 900, may optionally also have their color changed, e.g., to a gold color. Display 900 may also provide indications of physical attributes, e.g., current and impedance, for each active electrode. As shown, status bars 958 are provided indicating the instantaneous impedance at each electrode.

Figure 14:
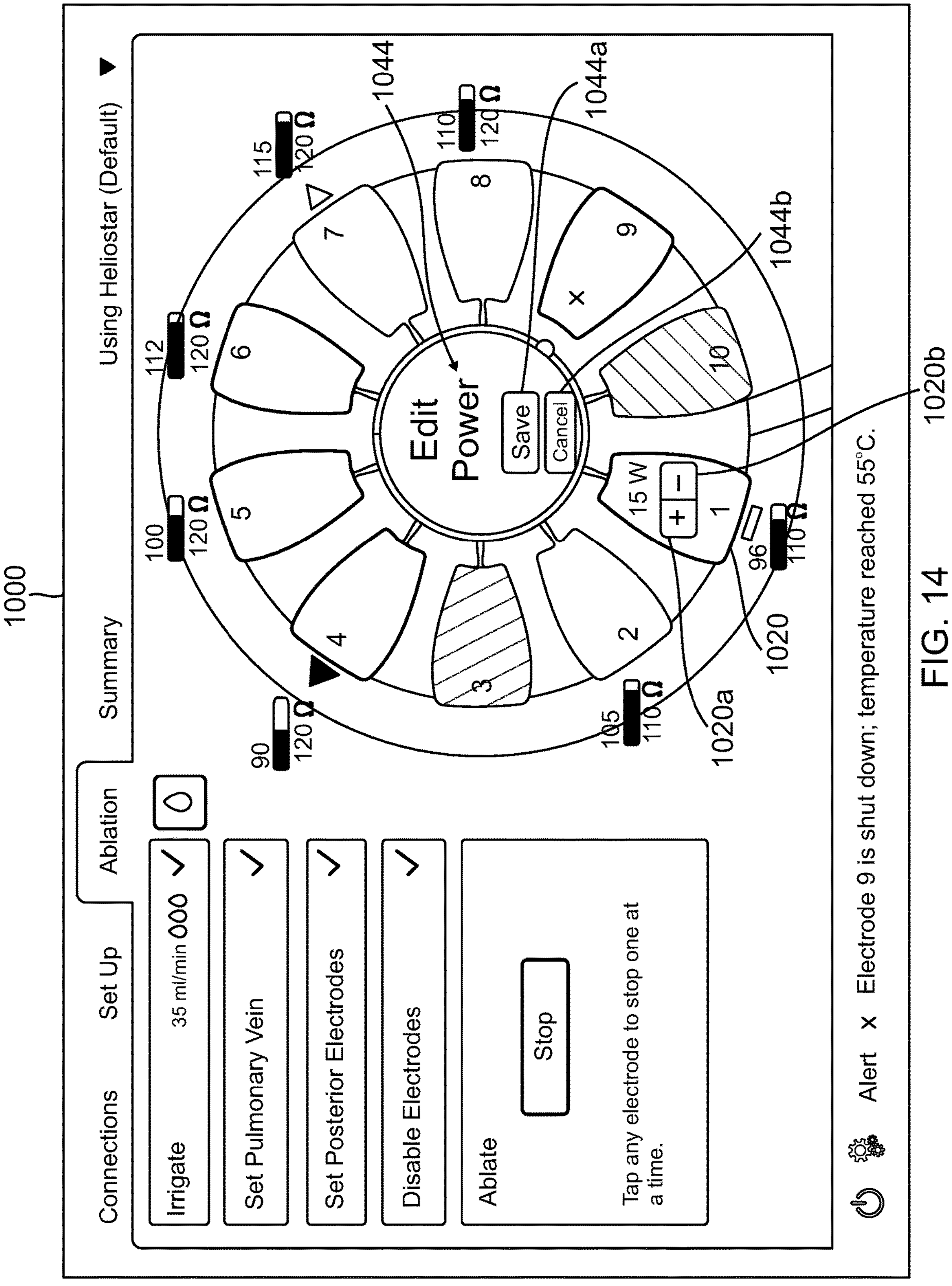
FIG. 14 is a tenth representation of a GUI display.

A tenth exemplary GUI display 1000 is reflected in FIG. 14. GUI display 1000 is similar to GUI display 900 except for the differences described herein. GUI display 1000, like GUI display 900, corresponds to a segment of the ablation process during which at least some of electrodes 33 have been activated. Specifically, GUI display corresponds to a mode in which the power supplied to each individual electrode may be modified. GUI display 1000 includes a control overlay comprising icons that professional 14 may use to communicate to processor 46 that the power being supplied to individual electrodes should be modified. As shown, electrode icon 1020, corresponding to the first electrode, includes an indication of the power (e.g., 15 watts) being supplied thereto. Electrode icon 1020 further includes an increase-power box **1020*a* and a decrease-power box 1020*b*, which may be touched or clicked by professional 14 to command processor 46 to increase or decrease the power being supplied to the electrode. After the desired power has been set, professional 14 can touch or click save box 1044*a* or cancel box 1044*b* to return to display 900**.

Figure 15:
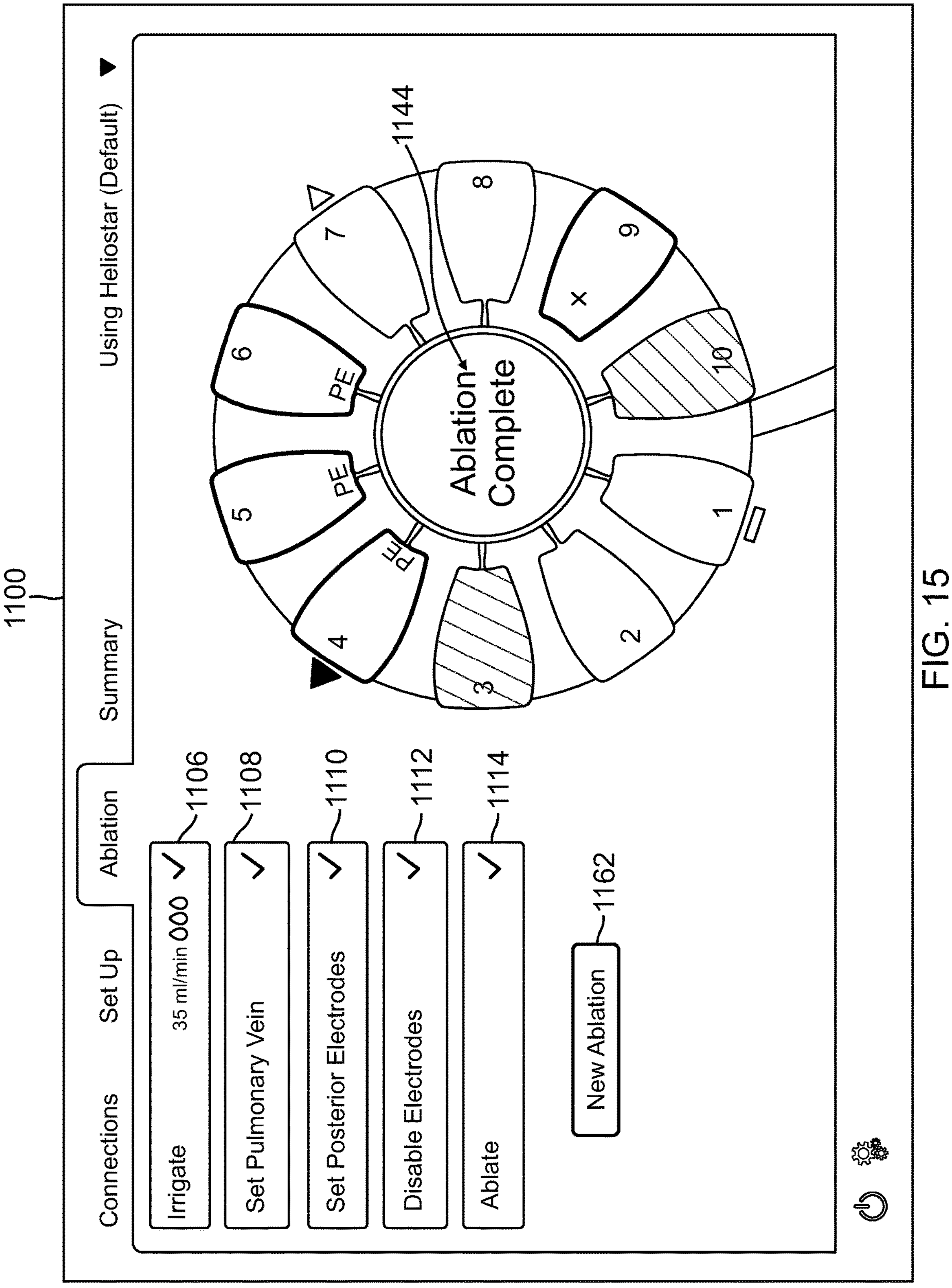
FIG. 15 is a eleventh representation of a GUI display.
Figure 16:
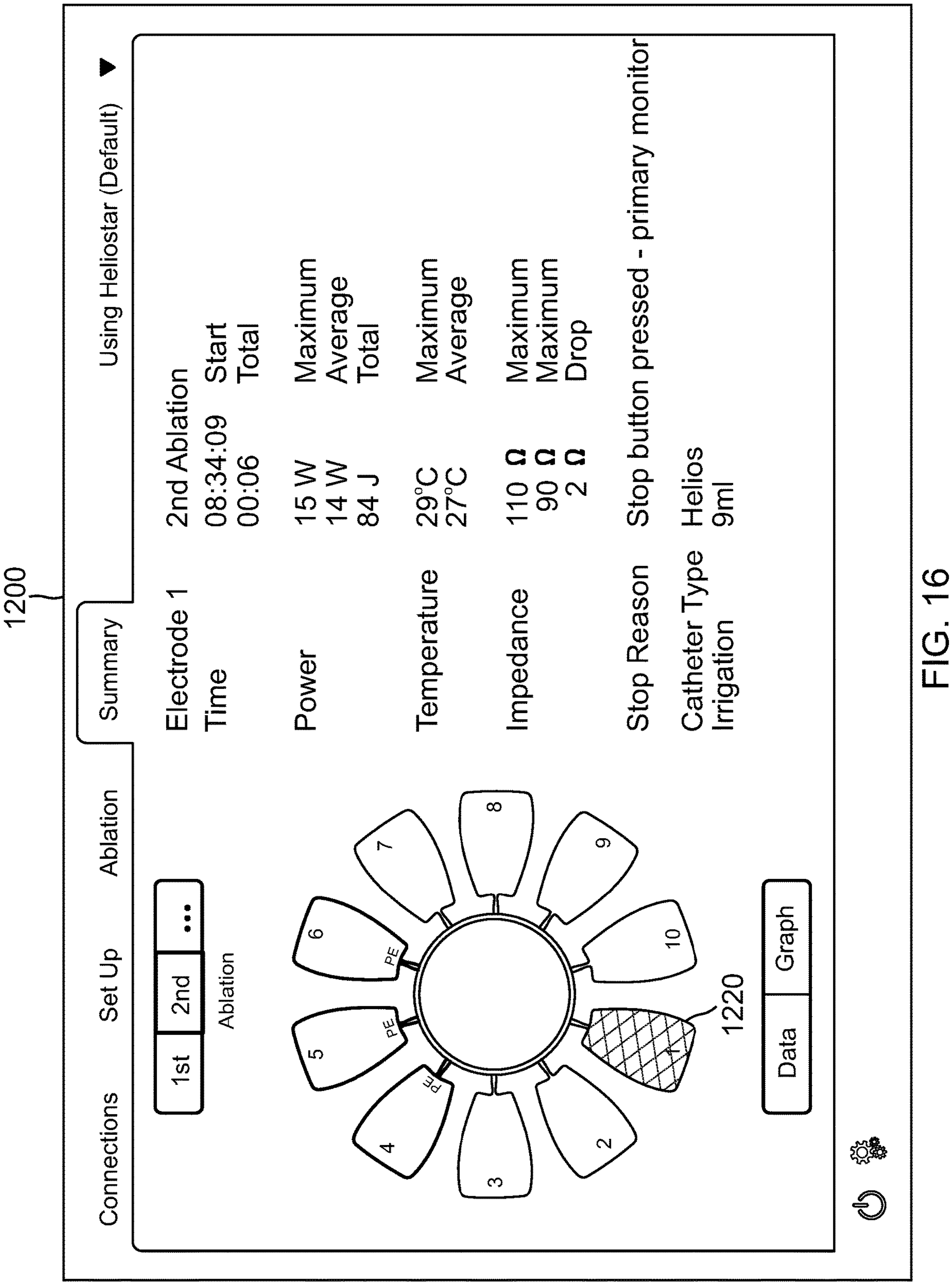
FIG. 16 is a twelfth representation of a GUI display.

An eleventh exemplary GUI display 1100 is reflected in FIG. 15. GUI display 1100 is similar to GUI display 900 except for the differences described herein. GUI display 1100 corresponds to a segment of the ablation procedure after all previously activated electrodes 33 have been deactivated. Accordingly, center portion 1144 may indicate a message, such as “Ablation Complete.” All dialog boxes 1106, 1108, 1110, 1112, and 1114 are shown in a collapsed configuration. An icon or box 1162 is provided that a surgeon may touch or click on to indicate to processor 46 that a new ablation procedure is to be performed A twelfth exemplary GUI display 1200 is reflected in FIG. 16. GUI display 1200 provides summary information or statistics of the ablation procedure for an electrode 33 that a professional 14 may find useful in making determinations of further therapy. As shown, electrode icon 1220 is highlighted such that the information provided corresponds to the first electrode.

Figure 17:
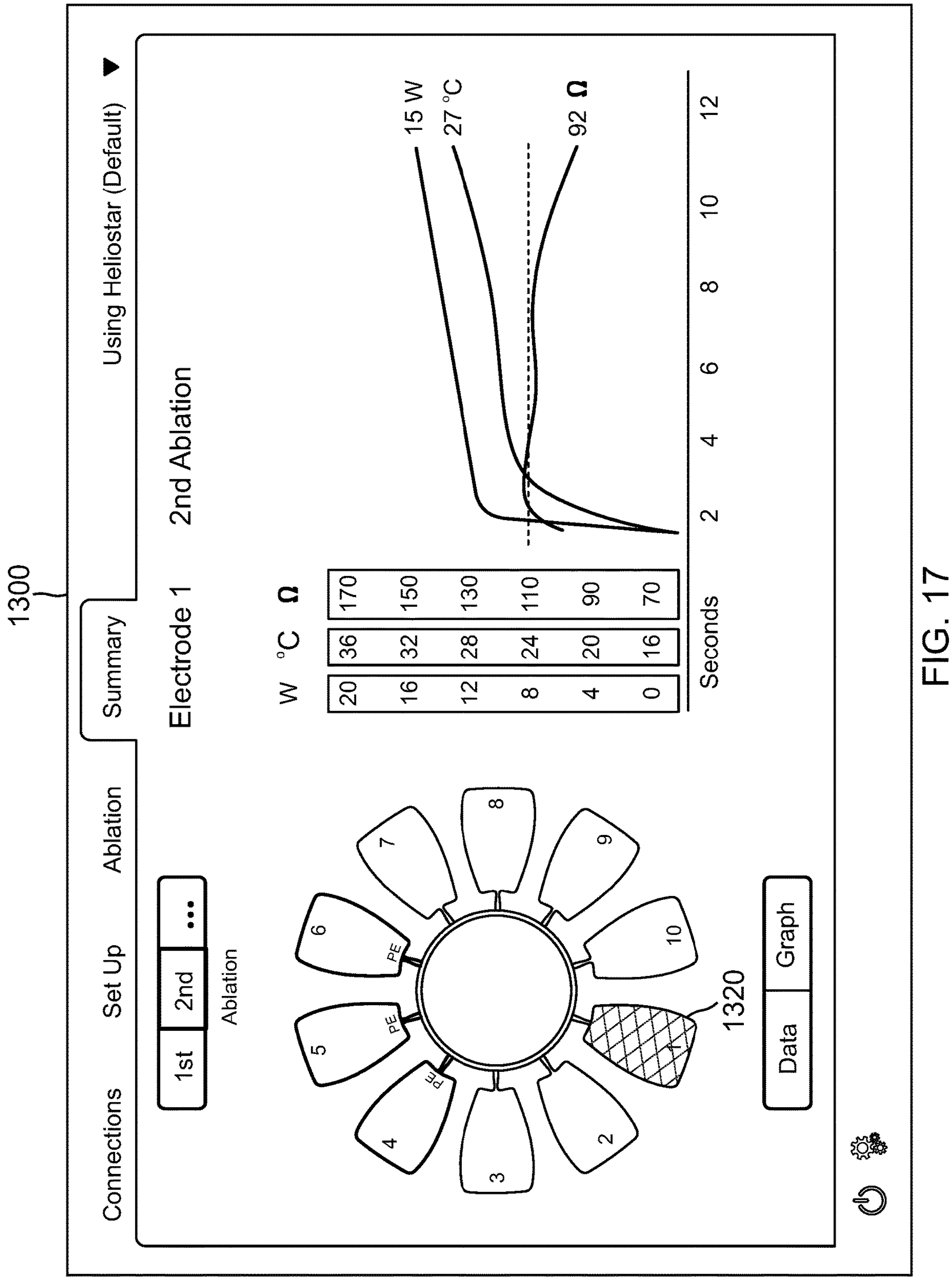
FIG. 17 is a thirteenth representation of a GUI display.
Figure 18:
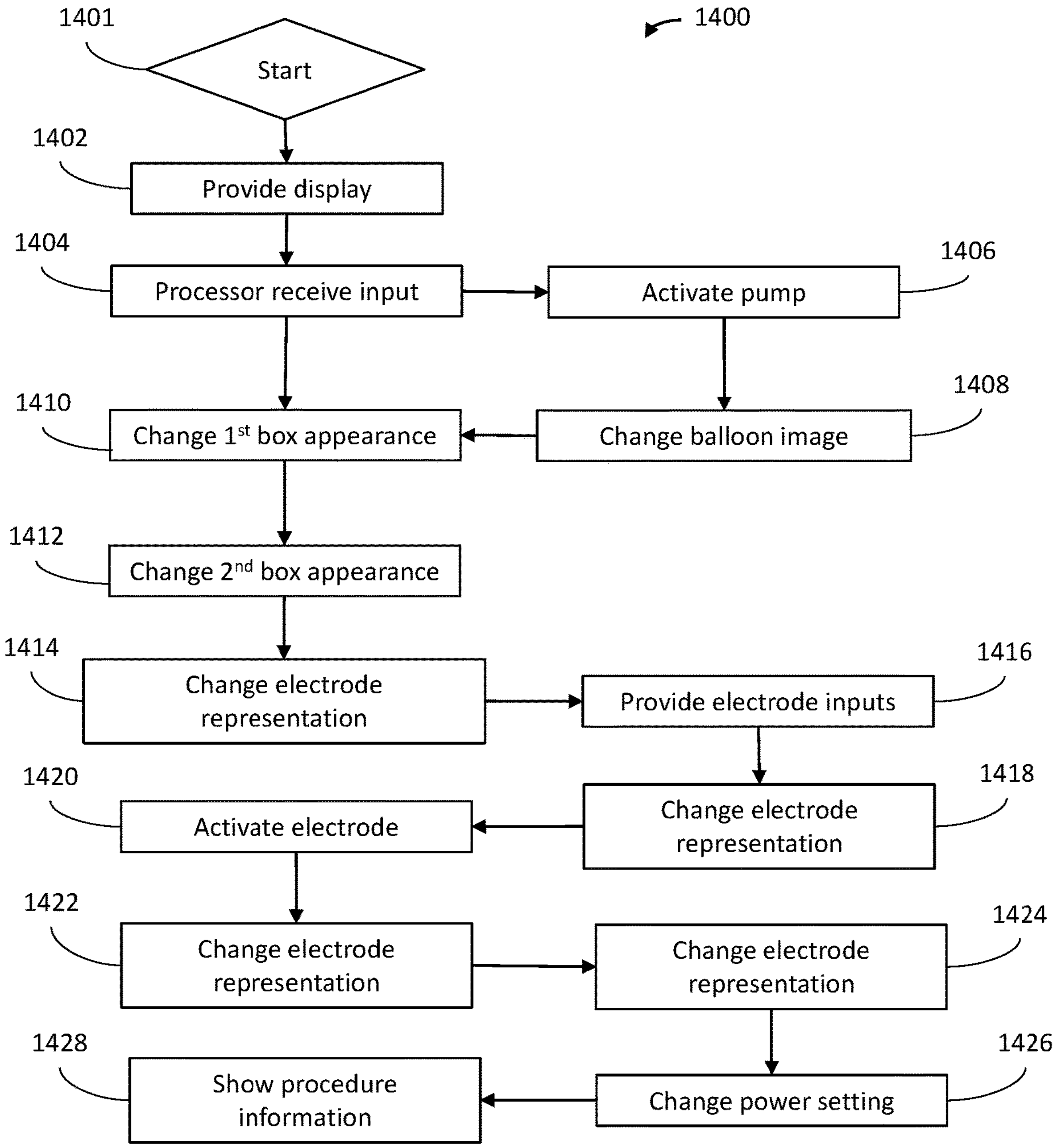
FIG. 18 is a flow chart for a method of using the GUI displays.

A thirteenth exemplary GUI display 1300 is reflected in FIG. 17. GUI display 1300 provides summary information or statistics of the ablation procedure for an electrode 33 that a professional 14 may find useful in making determinations of further therapy. As shown, electrode icon 1320 is highlighted such that the information provided corresponds to the first electrode.

Processor 46 may be further configured to change the display from among displays 100, 200, 300, 400, 500, 600, 700, 800, 900, 1000, 1100, 1200, and 1300 to another one of these displays, e.g., in sequential order based on inputs received from professional 14 via these displays or inputs received from sensors, e.g., temperature sensing members, of catheter 24. Thus, processor 46 may be configured to receive various inputs from a user interface device, such as screen 62 or console 49. Such inputs may include inputs sent to processor 46 when professional 14 touches screen 62 showing one of the aforementioned displays. For example, when professional 14 touches screen 62 in a location displaying a dialog box, e.g., dialog box 106, screen 62 may send a dialog-box input to processor 46. Similarly, when professional 14 touches screen 62 in a locations displaying an electrode icon, e.g., icon 426, screen 62 may send an electrode input to processor 46.

Dialog-box inputs may be generated from any of the dialog boxes, such as boxes 106, 108, 110, 112, and 114 on display 100 or their counterparts in other displays. For example, a dialog-box input could be professional 14 touching dialog box 106 in a closed configuration, which would cause an input from screen 62 to be sent to processor 46 that processor 46 would interpret as a command to change an appearance of dialog box 106, e.g., to expand dialog box 106. A dialog box-input could also be professional 14 touching dialog box 108 in a collapsed configuration, e.g., while dialog box 106 is in an expanded configuration. Processor 46 would receive an input from screen 62 based thereon, which processor 46 would interpret as a command to change an appearance of dialog boxes 106 and 108. For example, dialog box 106 could be placed into a collapsed configuration and dialog box 108 could be placed into an expanded configuration. This transition could correspond to, e.g., a transition from GUI display 100 to GUI display 200.

Dialog box inputs may also be considered inputs received by processor 46 based on professional 14 touching icons contained in the dialog boxes, e.g., icons **140*a*, 250*b*, 354 and 856. Thus, for example, when professional 14 touches icon 140*a*, screen 62 may send an input to processor 46 that processor 46 interprets as a command to display membrane representation 242, e.g., in display 200**.

Electrode inputs may be generated from any of the electrode icons, such as icons 420, 422, 424, 426, 428, 430, 432, 434, 436, and 438 on display 400 or their counterparts in other displays. For example, an electrode input could be professional 14 touching electrode icon 426, which would cause an input from screen 62 to be sent to processor 46 that processor 46 would interpret as a command to designate the fourth electrode 33 as a posterior electrode, and change its appearance to, e.g., that shown for electrode icon 526 on display 500.

Processor 46 may further be configured to prevent certain changes in appearance of the various displays, including dialog boxes and electrode icons, until after it has received certain inputs. Thus, for example, processor 46 may prevent, e.g., dialog box 108 from being change from a collapsed configuration to an expanded configuration until after it has received an input from, e.g., dialog box 106 or icon **140*a*. Accordingly, processor 46 may be configured to require that the various displays described herein are displayed in a set order, e.g., sequentially. For example, dialog box 108 can only be expanded to dialog box 208 after processor 46 has received a dialog-box input from dialog box 106 or icon 140*a*, and dialog box 310 can only be expanded to dialog box 410 after processor 46 has received a dialog-box input from dialog box 308 or icon 354**.

Additionally, processor 46 may be configured to change the appearance of electrode icons upon receiving a dialog-box input from screen 62. For example, when professional 14 touches ablate icon 856 and processor 46 receives a corresponding dialog-box input from screen 62, processor 46 would interpret it as a command to both activate a plurality of electrodes 33, but also change the appearance, e.g., color, of the corresponding electrode icons. Thus, for example, icon 832 could be white and then changed to icon 932 in gold, corresponding to a transition from display 800 to display 900.

Similarly, processor 46 may be configured to change the appearance of dialog boxes upon receiving an electrode input from screen 62. For example, when professional 14 touches electrode icon 426, and processor 46 receives a corresponding electrode input from screen 62, processor 46 would interpret it as a command to change the appearance of dialog box 410 to indicate that the fourth electrode has been set as a posterior electrode, as in dialog box 510.

Processor 46 may also be configured to display a measure of progress and change the appearance of that measure of progress. For example, as shown on display 100, a timer is shown in center portion 144 as indicating "0:00 of 60 sec." As shown on display 900, the timer in center portion 944 indicates "20 of 60 sec." Processor 46 may further be configured to increment the timer upon receiving a dialog-box input from ablate icon 856. Alternatively, or additionally, the elapsed time after icon 856 is touched may be reflected by, e.g., a scrubber bar as is sometimes found at the bottom of displays showing digital videos. In the embodiments disclosed herein, the dialog-box input provided to processor 46 when icon 856 is clicked may be considered the ultimate-dialog-box input because it is the last input processor 46 receives from the dialog boxes.

Dialog-box inputs and electrode inputs may also be received by processor 46 as commands to make further changes to system 12. For example, in response to receiving a dialog-box input from icon 140*a*, processor 46 may cause a pump to be activated.

By virtue of the embodiments illustrated and described herein, Applicant has devised a method and variations thereof for using a GUI of a computer system comprising a processor and a display (e.g., screen) to control a catheter that includes an expandable balloon disposed thereon. In particular, the method may be used to facilitate use of a catheter, such as catheter 24 having, among other things, a balloon 80 having a surface (e.g., membrane) and a plurality of electrodes 33 disposed on the surface, as described above, for performing a procedure, such as an ablation procedure in a heart of a subject. As reflected in the flow chart of FIG. 18, an exemplary method 1400 may be started at step 1401, and may include the additional following steps. At step 1402, a display may be provided as including a menu of dialog boxes, an image of a balloon with electrode representations, a measure of progress, and a global power. For example, at step 1402, screen 62 may be provided as showing, e.g., display 100 (FIG. 5), display 200 (FIG. 6), or display 300 (FIG. 7). Accordingly, at step 1402, a menu comprising a plurality of dialog boxes (e.g., a first dialog box, a second dialog box, and an ultimate dialog box) may be provided in a first sector of the display, and an image of the expandable balloon, including representations or icons of the electrodes (e.g., a first-electrode icon or representation) may be provided in a second sector of the display. At step 1404 the processor may receive an input from one of the dialog boxes, e.g., 106, 108, 208, 308, 310, 410, 412, 612, 712, and 814, in a closed or expanded configuration. For example, the processor may receive a first-dialog-box input from the first dialog box, a second-dialog-box input from the second dialog box, and an ultimate-dialog-box input from the ultimate dialog box. For purposes of referring to different variations of the method, it should be understood that the adjectives first, second, or ultimate do not refer to the position of the dialog box on a display, such that the first dialog box need not be limited to the top-most dialog box and the ultimate dialog box need not be limited to the bottom-most dialog box. Thus, for example, the first dialog box may be, e.g., dialog box 106, dialog box 108, dialog box 208, dialog box 310, or other dialog boxes. As such, the first-dialog-box input may vary correspondingly. For example, where the first dialog box is dialog box 106, the first dialog-box input could be a command received at processor 46 sent in response to professional 14 touching inflate box 140*a*. Further for example, where the first dialog box is dialog box 208, the-first-dialog-box input could be a command received at processor 46 sent in response to professional 14 touching second dialog box 108, shown in FIG. 5 in a closed configuration.

Inasmuch as the processor may be configured to receive multiple dialog-box inputs, variations of the method may additionally or alternatively include steps of receiving, at the processor, a first first-dialog box input from the first dialog box, a second first-dialog-box input form the first dialog box, a first second-dialog-box input from the second dialog box, a second second-dialog-box input from the second dialog box, a first third-dialog-box input from the third dialog box, a second third-dialog-box input from the third dialog box, a first ultimate-dialog-box input from the ultimate dialog box, and a second ultimate-dialog-box input form the ultimate dialog box. In these variations, the appearance of the first dialog box, the second dialog box, the third dialog box, the ultimate dialog box, any of the electrode representations, or any combination thereof, may be changed by the processor in response to receiving any of the aforementioned dialog box inputs. Preferably, these changes reflect transitioning from one GUI display to another.

In those variations where the first dialog box is dialog box 106 and the first dialog box input, which may be a first first-dialog-box input, is received at processor 46 because professional 14 touched inflate box 140*a*, the method includes steps 1406 and 1408. That is, upon receiving the command in response to professional 14 touching inflate box 140*a*, at step 1406, processor 46 may activate a pump at step 1406, which causes balloon 80 to expand. Correspondingly, at step 1408, the image of the balloon may be changed, e.g., by causing representation 242 of membrane 26 to appear on display 200 (FIG. 6) upon a transition from display 100 (FIG. 5), which does not show a representation of membrane 26.

Irrespective of which dialog box is the first dialog box referred to in the methods and variations, upon receiving the first dialog-box input, at step 1410 an appearance of the first dialog box is changed. For example, where the first dialog-box input is the command corresponding to professional 14 touching inflate box 140*a* of dialog box 106, a color of box 140*a* may be changed or a contour thereof highlighted. Further for example, where the first dialog-box input is the command corresponding to professional 14 touching dialog box 108 in the collapsed configuration, dialog box 108 may be expanded to become dialog box 208 upon a transition from display 100 (FIG. 5) to display 200 (FIG. 6).

At step 1412, which may be optional such that it need not be included in all variations of the methods described herein, an appearance of another or second dialog box may be changed in response to, e.g., automatically, receiving the first dialog-box input at processor 46. For example, where the first dialog box is dialog box 108, the second dialog box may be dialog box 106. Thus, first dialog box 106, shown in an expanded configuration on display 100 (FIG. 5) may be transitioned to a collapsed configuration corresponding to dialog box 206 on display 200 (FIG. 6). In those variations where the change to an appearance of the second dialog box is not automatic, professional 14 may cause the appearance of the second dialog box to change, e.g., by touching the second dialog box in a closed configuration, or touching another button or box contained in the second dialog box. For example, where the first dialog box is dialog box 106, and the second dialog box is dialog box 108, professional 14 could touch dialog box 108, thus causing screen 62 to send a first second-dialog-box input to processor 46, which processor 46 could interpret as a command to expand dialog box 108, transitioning it to dialog box 208 of display 200 (FIG. 6). As such, professional 14 would be prompted to identify to processor 46 the pulmonary vein that is to be ablated during the procedure by touching the corresponding box 250*a*, 250*b*, 250*c*, or 250*d*. Upon touching one of these boxes, screen 62 would provide a second second-dialog-box input to processor 46 informing it of the pulmonary vein to be ablated.

At step 1414, which may be optional such that it need not be included in all variations of the methods described herein, the electrode representations may each be changed, particularly after the balloon has been expanded (e.g., via box 106) and the pulmonary vein has been set (e.g., via box 208). For example, the color of each of the electrode representations may be changed. In further variations, this change may be simultaneous. The change to each of the electrode representations may be useful for indicating to professional 14 that the electrode representations may be used to send inputs from screen 62 to processor 46. That is, displays 100-300 (FIGS. 5-7) are configured to allow professional 14 to make inputs concerning irrigation and balloon position, but not to make inputs concerning electrode orientation of or power delivery to electrodes 33. As such, the electrode representations (e.g., 126, 128, 130 in FIG. 6) may be shown in, e.g., a gray color. However, display 400 (FIG. 8) concerns identification of those electrodes 33 that are located posteriorly relative to other electrodes, i.e., closer to a patient's esophagus than other electrodes. Professional 14 may identify the posterior electrodes to processor 46 by touching the electrode representations corresponding to those posterior electrodes. As such, the attention of professional 14 may be focused upon the electrode representations by changing their color to white in display 400 (FIG. 8) upon transitioning thereto from a display corresponding to an earlier portion of the method, such as display 300 (FIG. 7).

At step 1416, the electrode representations may be used to provide inputs to processor 46 concerning the orientation (e.g., relative position) of electrodes 33, the power to be delivered to electrodes 33, or both. For example, as noted with respect to step 1414, those electrodes 33 that are located posteriorly may be identified to the processor by touching the corresponding electrode representations. As such, upon professional 14 touching a first electrode representation, e.g., 426, a first first-electrode input may be sent from screen 62 to processor 46. Similarly, upon professional 14 touching other electrode representations, e.g., 428 and 430, first other-electrode inputs may be sent from screen 62 to processor 46. Alternatively or additionally, and with reference to displays 600 and 700 (FIGS. 10 and 11) professional 14 may touch at least one electrode representation to indicate to processor 46 that that electrode should be disabled, i.e., not be activated along with other electrodes that are to receive power for ablation.

At step 1418, the electrode representations may be changed to indicate that professional 14 touched them and that a corresponding input was sent to processor 46. For example, as seen on display 500 (FIG. 9), electrode representations 526, 528, and 530 have a thicker contour than do electrode representations 426, 428, and 430 on display 500 (FIG. 8). Moreover, electrode representations 526, 528, and 530 include a "PE" label, whereas electrode representations 426, 428, and 430 do not. As such, display 500 reflects that professional 14 indicated to processor 46 that fourth, fifth, and sixth electrodes 33, which correspond respectively to electrode representations 426, 428, and 430, as well as electrode representations 526, 528, and 530, are oriented posteriorly to the remaining electrodes 33, i.e., first through third electrodes 33 and seventh through tenth electrodes 33. Similarly, as seen on display 700 (FIG. 11), electrode representation 738 has been shaded to indicate to professional 14 that tenth electrode 33 has been disabled.

At step 1420, at least one of the electrodes 33 may be activated to ablate tissue. With reference to display 800 (FIG. 12) ablate box 856 may be touched by professional 14, e.g., for about two seconds, to activate at least one of the electrodes 33, i.e., all of them not disabled during step 1416.

At step 1422, the electrode representations may be changed again. This time, for example, they may be changed to indicate to professional 14 that they are receiving power for ablating tissue. Thus, for example, their color may be changed to, e.g., a gold color. For example, with reference to display 900, which corresponds to a segment of an ablation procedure where some of the electrodes 33 are receiving power, the corresponding electrode representations 920, 922, 926, 928, 930, 932, 934, and 936 may be shown in gold.

At step 1424, the electrode representations may be changed again. This time, for example, they may be changed to indicate to professional 14 that the power being delivered to each electrode 33 may be adjusted. For example, with reference to FIG. 14, electrode representation 1020 includes an indication of the power the first electrode 33 is receiving (shown as "15W" meaning "fifteen watts") and further includes plus and minus icons or boxes 1020*a* and 1020*b*.

At step 1426, professional 14 may change a power setting of any electrode. For example, again with reference to FIG. 14, professional 14 may raise the power first electrode 33 receives by touching plus box 1020*a* or may lower the power first electrode 33 receives by touching minus box 1020*b*.

At step 1428, information concerning the procedure may be shown on screen 62, e.g., display 1200 (FIG. 16), display 1300 (FIG. 17), or both. Professional 14 may review this information to determine whether a new round of ablation should be performed for the same pulmonary vein, or should be conducted on a different pulmonary vein, or whether the catheter should be removed from the subject.

To assist a medical professional in conducting an ablation procedure that employs the foregoing method, the GUI displays and the processor may function to prevent steps of the method from being performed prematurely. For example, the processor may be configured to prevent changing the appearance of the dialog boxes, the electrode representations, or any combination thereof. Thus, in further variations of the method, the processor may, e.g., prevent the change in the appearance of a second dialog box until it has received an input from the first dialog box, e.g., the first first-dialog-box input, which may be a command associated with box 140*a* to expand balloon 80.

Figure 19:
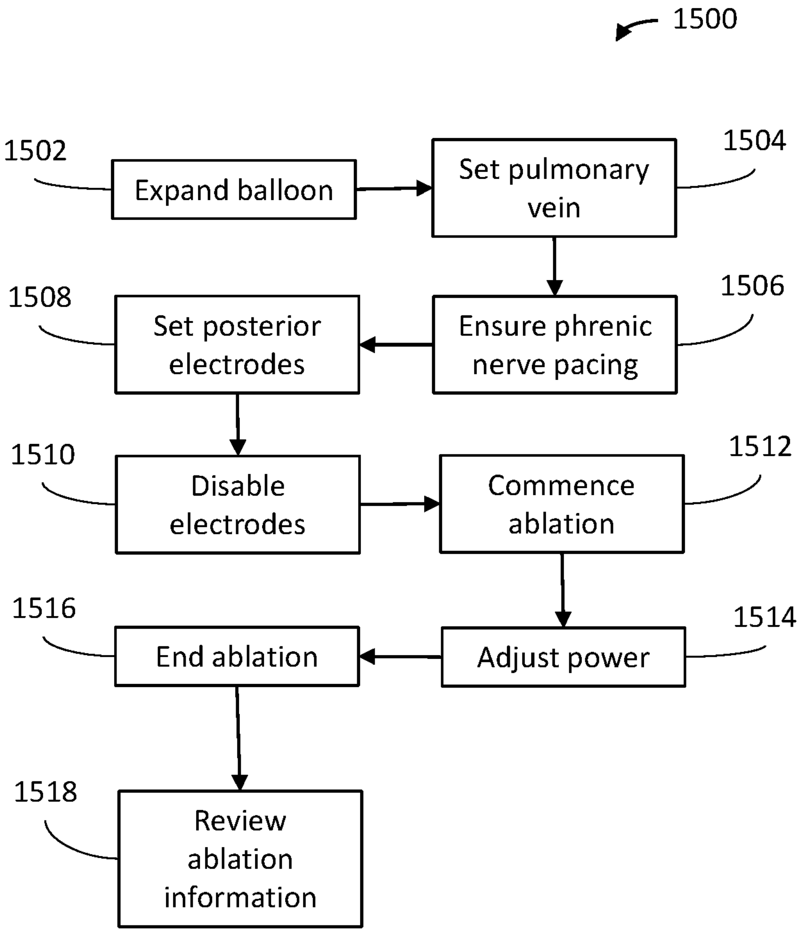
FIG. 19 is a flow chart for a method of ablating tissue.

Based on the foregoing, an ablation system comprising a catheter (e.g., 24), an operating console (e.g., 48) including a processor (e.g., 46) and screen (62), which may display GUI displays (e.g., the GUI displays described hereinabove), may be used by professional 14 to conduct an ablation procedure in, e.g., a heart of patient 18. FIG. 19 sets forth one such exemplary method 1500 with variations. Method 1500 begins after balloon 80, in a collapsed configuration, has been disposed in the heart of patient 18.

At step 1502, balloon 80 may be expanded by commencing irrigation through catheter 24 and balloon 80. That is, step 1502 may include any actions taken by professional 14 to cause an irrigation liquid to be pumped through catheter 24 and into balloon 80 at a sufficient flow rate to cause balloon 80 to expand. Display 100 (FIG. 5) is provided to assist professional 14 in performing step 1502 by prompting professional 14 to take two actions in dialog box 106. That is, dialog box 106 instructs: 1) "Pull plunger toward handle," alongside an image of a plunger on a handle of catheter 24; and 2) "Then, press inflate." As such, professional 14 may follow these instructions to pull the plunger of the catheter toward the handle, thus opening an irrigation lumen disposed through the catheter body to place balloon 80 in fluid communication with a source of an irrigation fluid (e.g., saline). Then, as instructed, professional 14 may touch inflate box 140*a* in dialog box 106 of display 100 (FIG. 5), which causes screen 62 to send a corresponding dialog-box input to processor 46, which processor 46 interprets as a command to activate a pump to flow the irrigation fluid from the source, through the catheter body, and into balloon 80. Accordingly, step 1502 ends after the pump has been activated and balloon 80 has been expanded.

At step 1504, professional 14 sets the pulmonary vein that will receive ablation therapy from the electrodes 33 on balloon 80 during an upcoming round of ablation performed in accordance with method 1500. That is, professional 14 informs processor 46 of the pulmonary vein into which balloon 80 will be disposed—or more specifically, the pulmonary-vein ostium into which balloon 80 will be disposed. Step 1504 may be commenced upon expansion of dialog box 108 from a collapsed configuration to an open configuration. As discussed above, such may occur automatically upon dialog box 106 being collapsed, or upon professional 14 touching dialog box 108. In either variation, processor 46 receives an input from screen 62 to expand dialog box 108, such as via a transition to display 200 (FIG. 6), which includes dialog box 208.

Dialog box 208 may include an instruction for professional 14 to "Set Pulmonary Vein" as well as pulmonary-vein icons or boxes 250*a*, 250*b*, 250*c*, and 250*d*, which correspond respectively to each of the four pulmonary veins as described above. As such, professional 14 may touch one of boxes 250*a*, 250*b*, 250*c*, and 250*d*, to cause screen 62 to send a corresponding dialog-box input to processor 46 identifying the chosen pulmonary vein.

In further variations of method 1500, at optional step 1506, upon receiving the dialog-box input indicating the chosen pulmonary vein, processor 46 may cause screen 62 to transition from display 200 (FIG. 6) to display 300 (FIG. 7), which includes dialog box 308 as having a confirmation icon or box 354 that includes an instruction "Ensure phrenic nerve pacing." Processor 46 may require receipt of a dialog box input sent by screen 62 in response to professional 14 touching box 354 before it will allow method 1500 to continue further. As such, box 354 serves as a reminder to the surgeon to check that phrenic nerve pacing has been enabled, and as a safety feature to prevent any ablation from occurring until professional 14 indicates that she has activated this pacing.

At step 1508, professional 14 sets the posterior electrodes. That is, professional 14 communicates to processor 46 those electrodes 33 that are located posteriorly in the patient, particularly relative to the other electrodes. Such indication may be helpful to avoid accidental ablation of the patient's esophagus. Step 1508 may commence upon expansion of dialog box 310 in display 300 (FIG. 7) to dialog box 410 in display 400 (FIG. 8). This transition may be caused by processor 46 upon receipt of a dialog box input corresponding to professional 14 having touched any of boxes 250*a-d* and perhaps also box 354. Alternatively, this transition may be caused by processor 46 upon receipt of a dialog box input corresponding to professional 14 touching box 310 in a closed configuration, e.g., after having touched any of boxes 250*a-d* and having or having not touched box 354.

The transition from display 300 to display 400 may also include changing the electrode representations, e.g., from gray to white. This change may prompt professional 14 to indicate her determinations of which electrodes are disposed posteriorly to processor 46 by touching the corresponding electrode representations on display 400. Accordingly, processor 46 may accept electrode inputs from screen 62 showing display 400 with white electrode representations, whereas, in preferred variations of the method, it would not when screen 62 was showing displays 100, 200, and 300 with gray electrode representations.

With display 400 on screen 62, professional 14 may touch those electrode representations corresponding to the electrodes 33 disposed posteriorly. For each electrode representation she touches, a corresponding electrode input may be sent from screen 62 to processor 46 informing processor 46 of the selection. In response, processor 46 may, among other things, further change an appearance of the electrode representation to confirm the selection and, during later steps of the method, remind professional 14 of the selection. In the example reflected in display 400 (FIG. 8) and display 500 (FIG. 9) professional 14 determined that fourth, fifth, and sixth electrodes 33 were the posterior electrodes and touched electrode representations 426, 428, and 430, thus causing screen 62 to send corresponding electrode inputs to processor 46, which further causes processor 46 to change the appearance of these electrode representations to that of electrode representations 526, 528, and 530. For example, as shown on display 500, their contours may be thickened and they may be labeled "PE" for "posterior electrode." Further, upon receiving these electrode inputs from screen 62, processor 46 may change the appearance of dialog box 410 to that of dialog box 510, e.g., to provide a textual confirmation and reminder of the selections. As shown, dialog box 510 indicates "you have set 4, 5, & 6."

At step 1510, the GUI provides professional 14 with an option to disable any of electrodes 33, such that the disabled electrodes will not receive power while non-disabled electrodes receive power during forthcoming steps 1512, 1514, and 1516. Step 1510 is carried out in a manner similar to step 1508. That is dialog box 412 may be expanded to become dialog box 612 following processor 46 receiving dialog box inputs from screen 62, e.g., professional 14 touching dialog box 412. As shown, dialog box 12 includes a textual prompt for professional 14 to "Tap any electrode on the balloon to turn it off before ablation." As such, those electrodes to be disabled may be identified to processor 46 by professional 14 touching the electrode representations corresponding the electrodes to be disabled. In the example reflected in display 600 (FIG. 10) and display 700 (FIG. 11), professional 14 determined that tenth electrode 33 should be disabled and touched the corresponding electrode representation. This caused screen 62 to send a corresponding electrode input to processor 46 to disable tenth electrode 33. In response, processor 46 caused the electrode representation to change, e.g., to be grayed out as seen at 738. Further, upon receiving these electrode inputs from screen 62, processor 46 may change the appearance of dialog box 612 to that of dialog box 712, e.g., to provide a textual confirmation or reminder of the selections. As shown, dialog box 712 indicates "you have disabled 10."

The ablation segment of the method is next performed, beginning at step 1512, i.e., a commence-ablation step. Step 1512 may comprise professional 14 touching, e.g., dialog box 614 of display 600 (FIG. 10) to cause screen 62 to send a dialog-box input to processor 46, which processor 46 interprets as a command to expand dialog box 614 to dialog box 814 of display 800 (FIG. 12). Dialog box 814 includes ablate box 856 and instructs beneath "Hold for 2 sec." As such, dialog box 814 prompts professional 14 to activate electrodes 33 by depressing box 856, but prevents inadvertent activation by requiring that the box be contacted for at least a certain amount of time, e.g., at least about two seconds. Upon processor 46 receiving a dialog box input from screen 62 corresponding to two seconds of holding box 856, processor 46 activates all electrodes that were not disabled during step 1510.

Power is delivered to the non-disabled electrodes 33 on balloon 80 for a duration of time, e.g., sixty seconds. During this time, step 1514 may optionally be performed to adjust the power being delivered to one or more of the active electrodes. Four exemplary adjustments are explained here. All, some, or none may be performed. First, with reference to display 900 (FIG. 13), dialog box 914 includes a stop box 956. Professional 14 may touch stop box 956 to cease all power delivery to all of the active electrodes. That is, upon touching stop box 956, screen 62 sends a dialog-box input to processor 46 that processor 46 interprets as a command to cease the power delivery to all of the electrodes. In some variations of the method, touching stop box 956 causes the ablation segment of the method to end, which is also one way of performing the end-ablation step 1516. In other variations of the method, touching stop box 956 causes display 900 (FIG. 13) to transition back to display 800 (FIG. 12), such that step 1512 may be performed anew.

Concerning the second adjustment, box 914 instructs "Tap any electrode to stop one at a time." As such, should professional 14 determine that any of electrodes 33 should be deactivated, she may touch the corresponding electrode representation to disable the electrode. As seen on display 900, she has touched electrode representation 924, indicating that she determined that third electrode 33 should be disabled. By touching electrode representation 924, screen 62 sends an electrode input to processor 46 that processor 46 interprets as a command to cease further power delivery to third electrode 33.

Concerning the third adjustment, processor 46 may determine that certain electrodes 33 should be automatically disabled upon a determination that the temperatures of those electrodes may have exceeded a safety maximum. In such instances, processor 46 may cause the corresponding electrode representation to be changed. For example, display 900 reflects that ninth electrode 33 has been disabled for exceeding a safety maximum by showing electrode representation 936 with a thickened contour and perhaps also with its color changed to, e.g., red. Further, an X may be provided on electrode representation 936. Additionally, connection 836*a* of display 800 (FIG. 12) may be removed. Also a textual indication may be provided, e.g., an alert is shown at the bottom of display 900 indicating "Electrode 9 is shut down; temperature reached 55° C."

Concerning the fourth adjustment, display 1000 (FIG. 14) may be provided upon professional 14 commanding processor 46 to enter an "Edit Power" mode, for example by touching center portion 944 of the balloon representation. In the "Edit Power" mode of display 1000, an control overlay may be provided over the electrode representations. Although only one such overlay is provided on display 1000, i.e., over electrode representation 1020, it should be understood that a control overlay could be provided over some or all of the electrode representations corresponding to the active electrodes 33. As noted above, the control overlay comprises boxes or icons 1020*a* and 1020*b* that professional 14 may use to communicate to processor 46 that the power being supplied to individual electrodes should be modified. Upon touching these boxes, electrode inputs are provided by screen 62 to processor 46, which processor 46 interprets as commands to increase or decrease the power being supplied to the electrode, e.g., first electrode 33 as shown. After the desired power has been set, professional 14 can touch or click save box 1044*a* or cancel box 1044*b* to return to display 900.

After power has been provided to electrodes 33 for a duration of time, e.g., about sixty seconds, the ablation segment automatically ends at step 1516 where processor 46 automatically deactivates electrodes 33. With reference to display 1100 (FIG. 15), center portion 1144 may indicate "Ablation Complete." Further, new-ablation box 1162 may be provided. Professional 1162 may touch box 1162 to return to display 500 (FIG. 9) and step 1502. For example, professional 14 may have determined that the same pulmonary vein should receive another round of ablation therapy, discussed below with reference to step 1518, or that a different pulmonary vein should receive ablation therapy.

At step 1518, professional 14 determines whether the same pulmonary vein should receive another round of ablation therapy. This step comprises professional 14 reviewing information concerning the completed round of ablation. Such information may be provided as textual data in the form of display 1200 (FIG. 16) or as graphical data in display 1300 (FIG. 17). The summaries provided may be cumulative of any rounds of ablations previously conducted. Thus, for example, display 1200 and display 1300 both reflect that two rounds of ablations have been performed as indicated in the upper left by boxes "1st" and "2nd." As shown, the "2nd" box includes a thickened contour, indicating that the information reflected on the display corresponds to the second round of the ablation. Furthermore, electrode representations 1220 and 1320 are highlighted further indicating that the information reflected on the display corresponds to the first electrode 33 during the second round of ablation. Professional 14 may thus command processor 46 to display information corresponding to a round of ablation and each electrode by making the appropriate selections on displays 1220 and 1320.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A method of using a graphical user interface (GUI) of a computer system comprising a processor and display to control a catheter including an expandable balloon disposed thereon, the expandable balloon including a surface and a plurality of electrodes comprising a first electrode disposed thereon, the method comprising:

providing in a first sector of the display, a menu comprising a first dialog box, a second dialog box, and an ultimate dialog box;

providing in a second sector of the display, an image of the expandable balloon comprising a plurality of electrode representations including a first-electrode representation;

receiving at the processor a first first-dialog-box input from the first dialog box;

after the operation of receiving at the processor the first first-dialog-box input from the first dialog box, receiving at the processor a first second-dialog-box input from the second dialog box;

in response to the operation of receiving at the processor the first second-dialog-box input from the second dialog box, changing both a first-dialog-box appearance of the first dialog box and a second-dialog-box appearance of the second dialog box, in which the first-dialog-box appearance is changed from a first-dialog-box expanded configuration to a first-dialog-box collapsed configuration, and in which the second-dialog-box appearance is changed from a second-dialog-box collapsed configuration to a second-dialog box expanded configuration;

receiving at the processor a first first-electrode input from the first-electrode representation; and changing the first-electrode representation.

2. The method of claim 1, further comprising changing the image of the balloon.

3. The method of claim 1, in which at least one of the plurality of electrode representations includes an alphanumeric indicator.

4. The method of claim 1, in which at least one of the plurality of electrode representations includes a shape indicator.

5. The method of claim 1, further comprising changing the appearance of each of the plurality of electrode representations.

6. The method of claim 5, in which the appearance of each of the plurality of electrode representations is changed simultaneously.

7. The method of claim 1, further comprising activating at least one of the plurality of electrodes.

8. The method of claim 7, further comprising displaying a measure of progress.

9. The method of claim 8, in which the measure of progress comprises a timer.

10. The method of claim 8, further comprising displaying a global power.

11. The method of claim 7, further comprising second changing the first-electrode representation.

12. The method of claim 11, further comprising third changing the first-electrode representation.

13. The method of claim 12, further comprising activating a pump to cause an irrigation fluid to expand the expandable balloon.

14. The method of claim 12, in which the first first-electrode input comprises a command to designate the first electrode as being disposed posteriorly to at least another electrode of the plurality of electrodes.

15. The method of claim 12, further comprising changing a power setting corresponding to the first electrode.

16. The method of claim 15, in which the plurality of electrodes further comprises a second electrode; and the plurality of electrode representations further comprises a second-electrode representation.

17. The method of claim 16, further comprising:

receiving at the processor a first second-electrode input; and changing the second-electrode representation.

18. The method of claim 17, further comprising second changing the second-electrode representation.

19. The method of claim 18, further comprising third changing the second-electrode representation.

20. The method of claim 19, in which the first second-electrode input comprises a command to designate the second electrode as being disposed posteriorly to at least another electrode of the plurality of electrodes.

21. The method of claim 20, in which the at least another electrode comprises the first electrode.

* * * * *